United States Patent
Zhang et al.

(10) Patent No.: US 11,864,999 B2
(45) Date of Patent: Jan. 9, 2024

(54) SHEATH FOR DELIVERING INTERVENTIONAL INSTRUMENT AND SHEATH ASSEMBLY

(71) Applicant: VENUS MEDTECH (HANGZHOU), INC., Zhejiang (CN)

(72) Inventors: Zhifei Zhang, Hangzhou (CN); Jianan Wang, Hangzhou (CN); Yu Zhang, Hangzhou (CN); Zhenjun Zi, Hangzhou (CN); Frank Min Zeng, Irvine, CA (US); Hou-Sen Lim, Singapore (SG)

(73) Assignee: Venus Medtech (Hangzhou) Inc, Hangzhou (CN)

( * ) Notice: Subject to any disclaimer, the term of this patent is extended or adjusted under 35 U.S.C. 154(b) by 251 days.

(21) Appl. No.: 17/237,344

(22) Filed: Apr. 22, 2021

(65) Prior Publication Data
US 2022/0000615 A1   Jan. 6, 2022

(30) Foreign Application Priority Data

Jul. 6, 2020   (CN) .......................... 202010639551.8
Apr. 19, 2021   (CN) .......................... 202110418891.2

(51) Int. Cl.
*A61F 2/24*   (2006.01)

(52) U.S. Cl.
CPC .... *A61F 2/2436* (2013.01); *A61F 2210/0076* (2013.01)

(58) Field of Classification Search
CPC ............ A61F 2/2436; A61F 2210/0076; A61F 2/962; A61F 2002/9623; A61M 25/0144; A61B 17/3417
See application file for complete search history.

(56) References Cited

U.S. PATENT DOCUMENTS

| | | | |
|---|---|---|---|
| 6,214,036 B1* | 4/2001 | Letendre et al. ......... | A61F 2/07 |
| 2007/0112355 A1* | 5/2007 | Salahieh et al. ...... | A61F 2/2418 |
| 2011/0098804 A1* | 4/2011 | Yeung ................... | A61F 2/2412 |
| | | | 623/2.1 |
| 2014/0012368 A1* | 1/2014 | Sugimoto et al. . | A61B 17/0057 |
| 2016/0220370 A1* | 8/2016 | Savage et al. ........ | A61F 2/2427 |
| 2016/0317301 A1* | 11/2016 | Quadri et al. ......... | A61F 2/2436 |
| 2019/0008639 A1* | 1/2019 | Landon et al. ......... | A61F 2/243 |
| 2019/0008640 A1* | 1/2019 | Cooper ................. | A61F 2/2436 |
| 2020/0397575 A1* | 12/2020 | Liu et al. .............. | A61F 2/2436 |

* cited by examiner

Primary Examiner — Tan-Uyen T Ho
Assistant Examiner — Theodore Le Vu
(74) Attorney, Agent, or Firm — Raymond Sun

(57) ABSTRACT

The present invention discloses a core assembly, a sheath assembly, a sheath, a sheath processing method and an interventional instrument delivery system and method. A core assembly for delivering an interventional instrument according to the present invention comprises a core tube, a locking member fixed at a distal end of the core tube for connecting the interventional instrument, and a bendable adjustable tube mounted around an outer periphery of the core tube, wherein the distal ends of the bendable adjustable tube and the core tube are fixedly connected to each other, and the proximal ends can slide relative to each other.

19 Claims, 17 Drawing Sheets

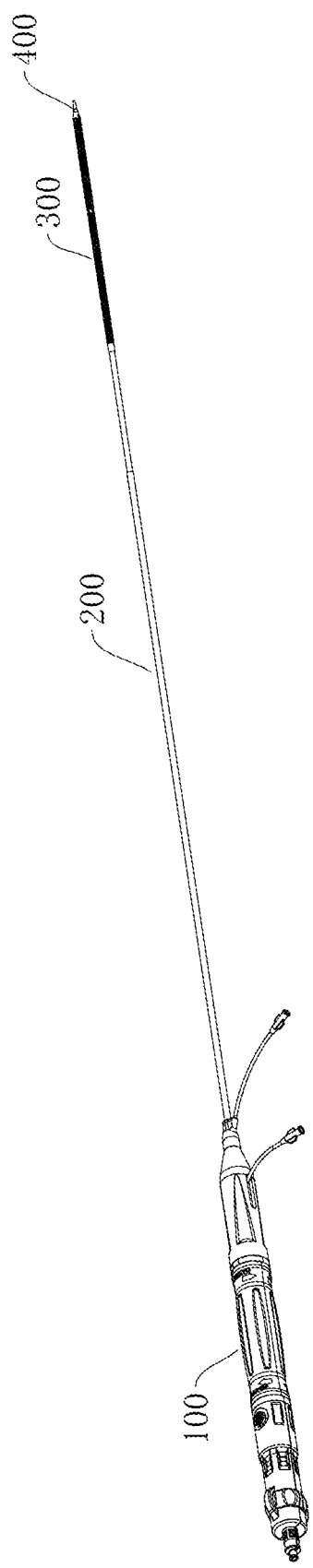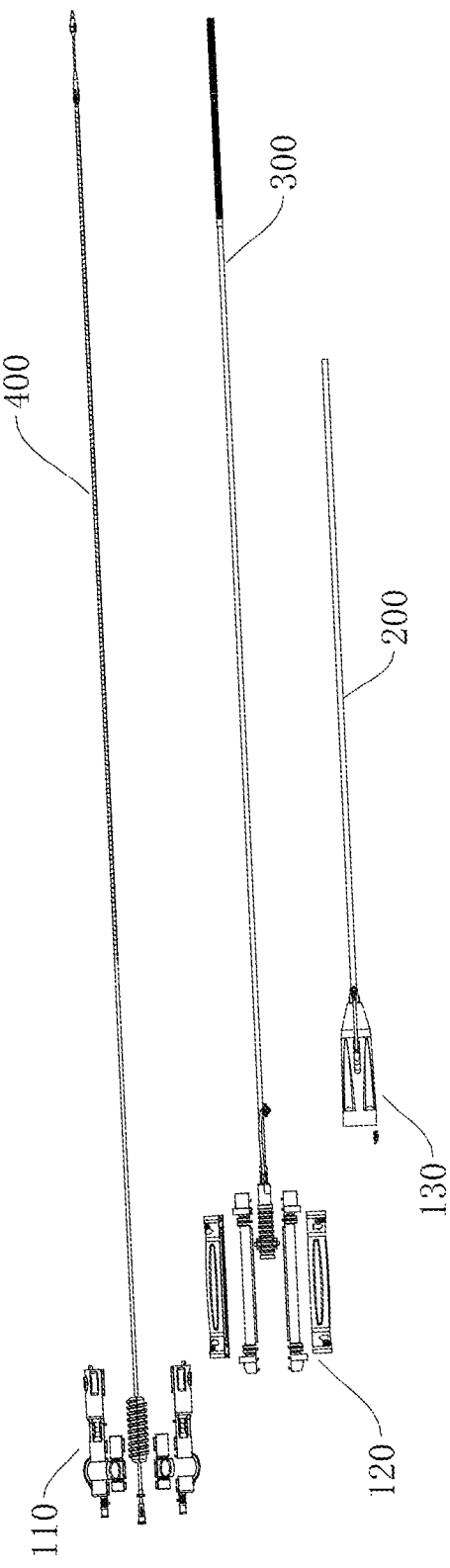

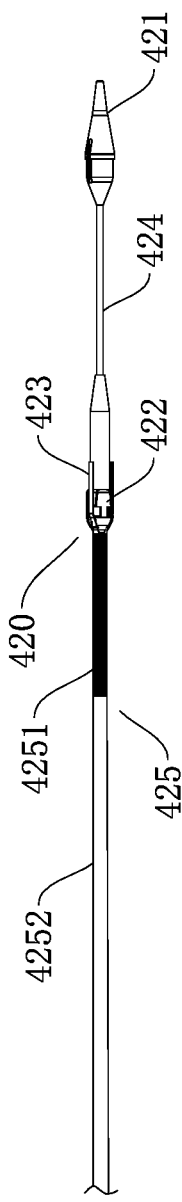
FIG. 5c
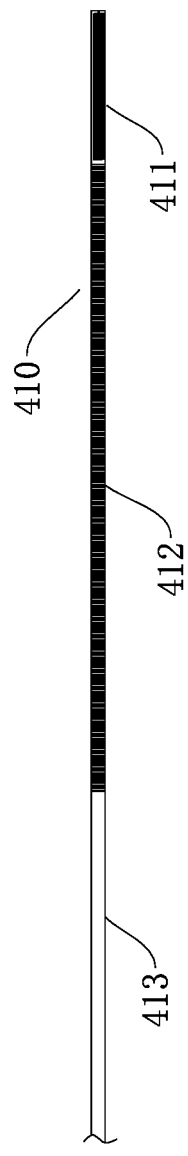
FIG. 6
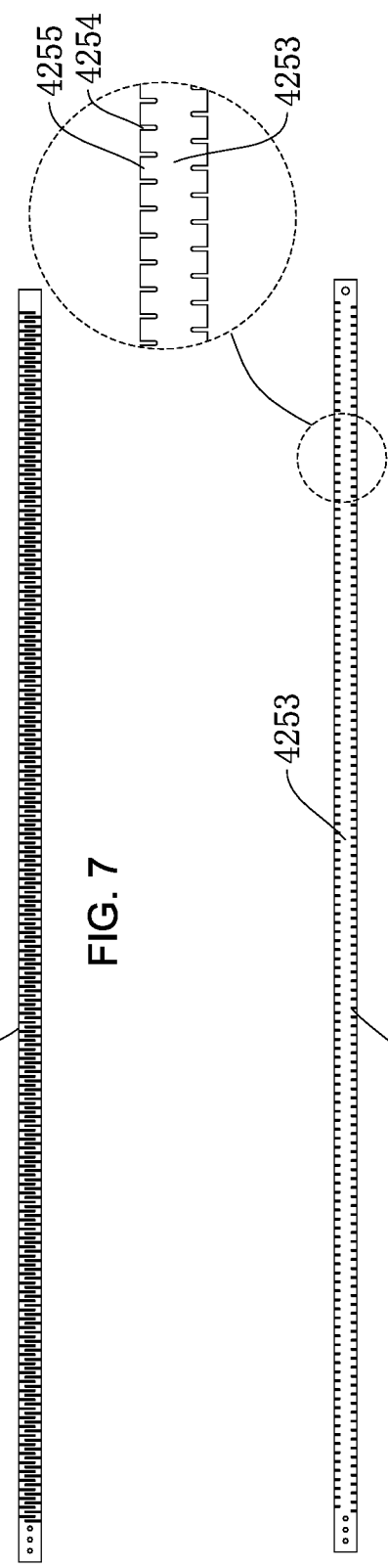
FIG. 7
FIG. 8

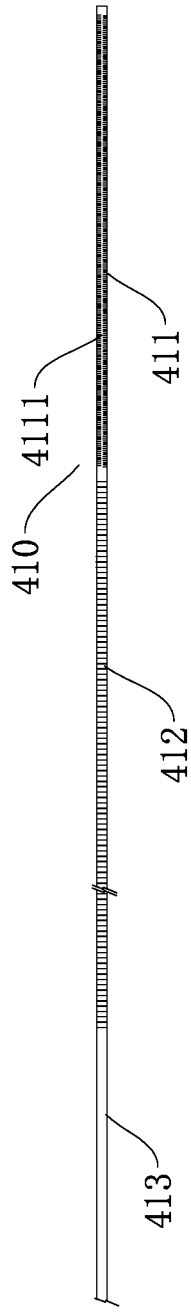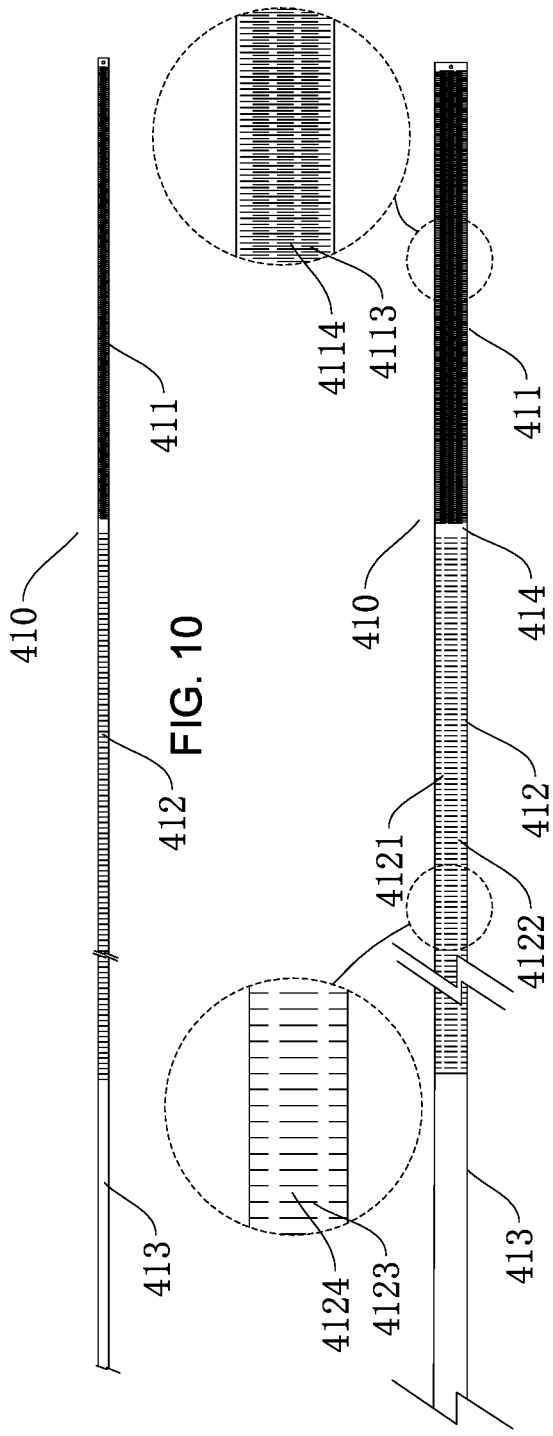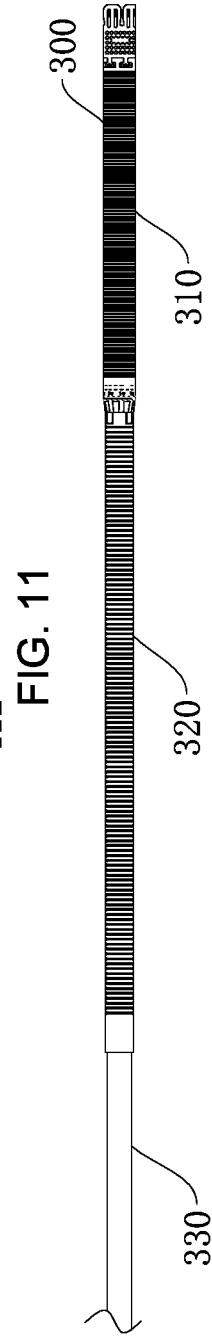

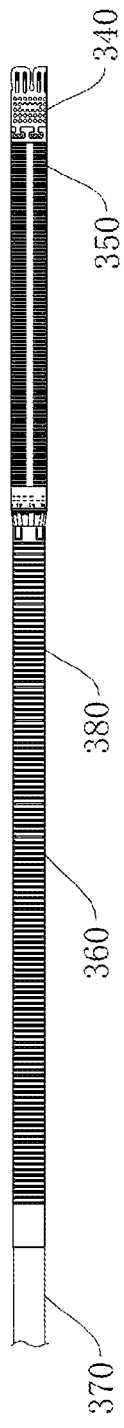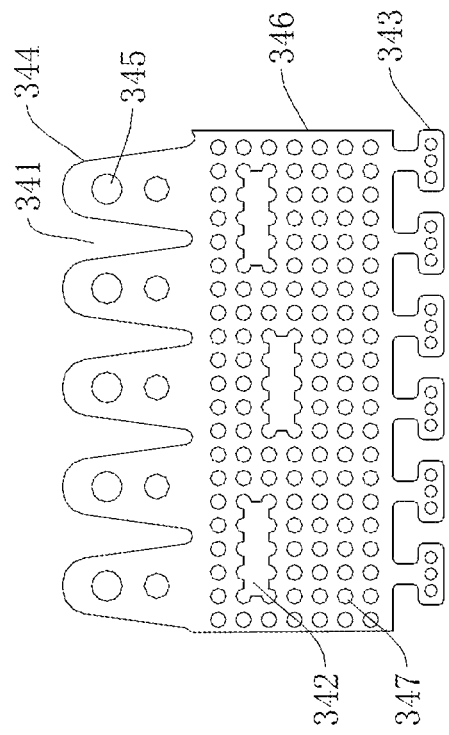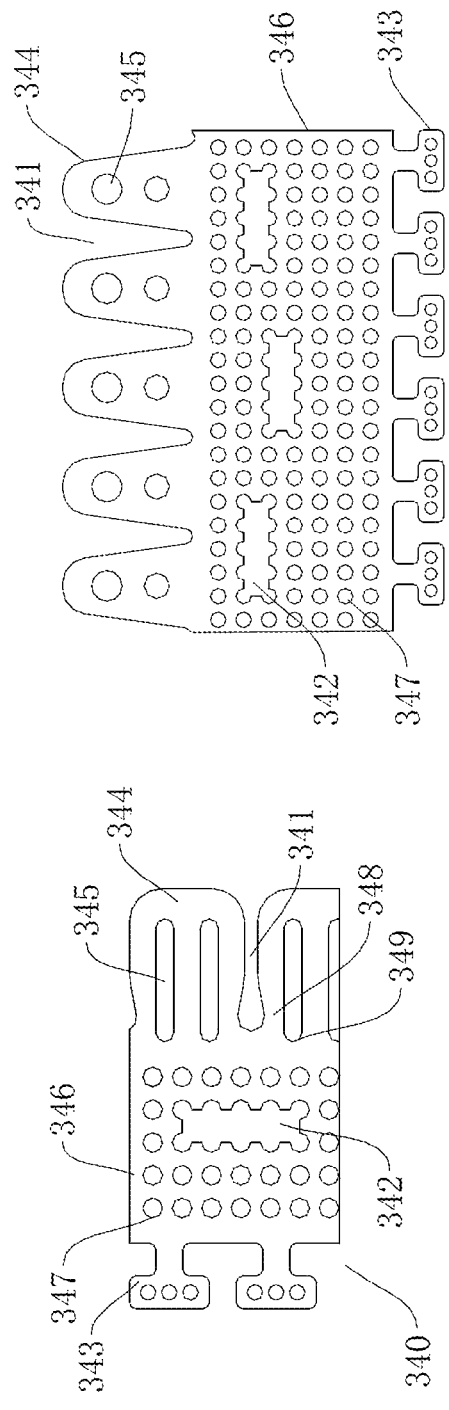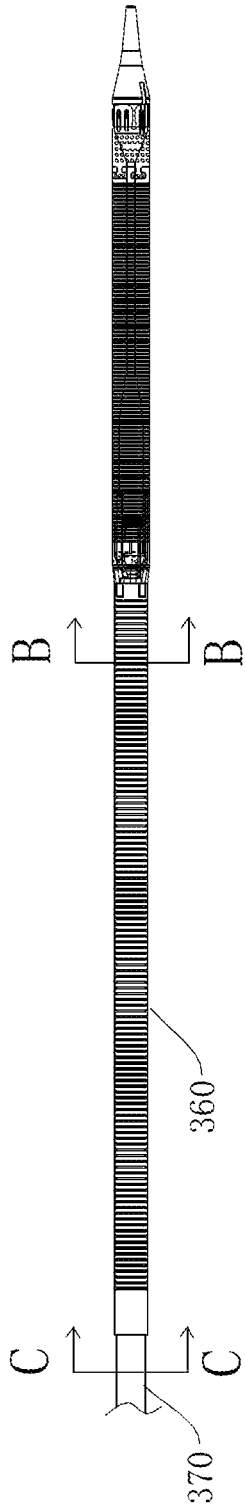
FIG. 18
FIG. 19a
FIG. 19b
FIG. 20

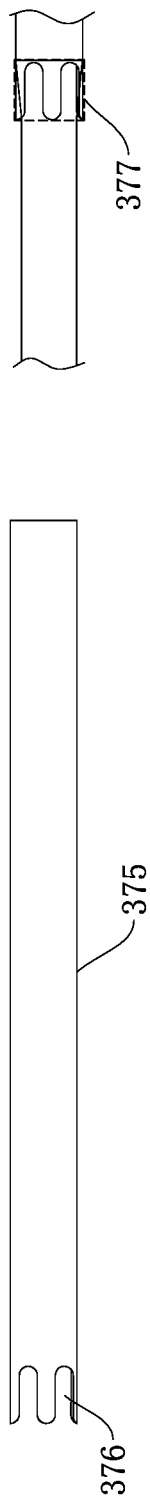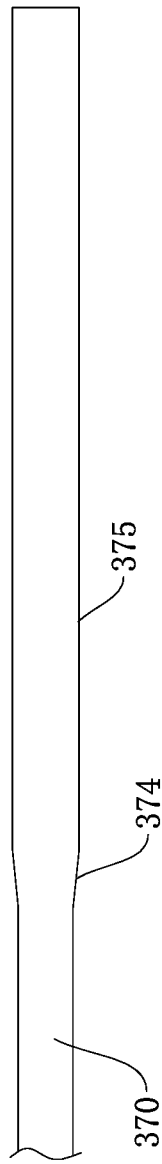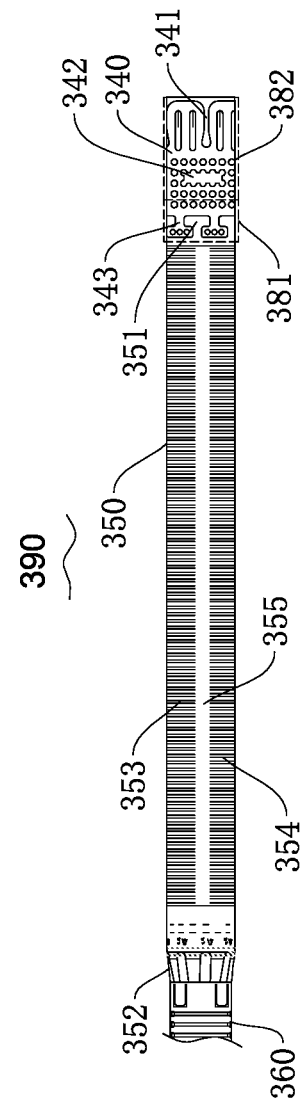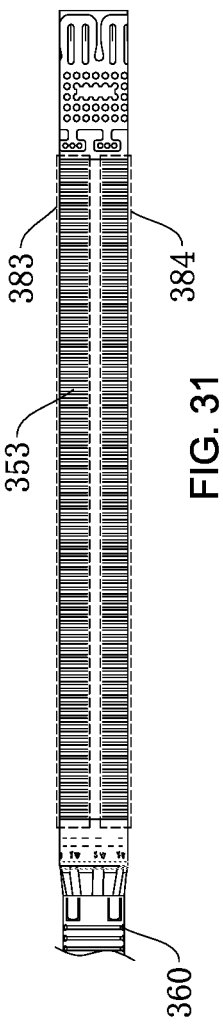

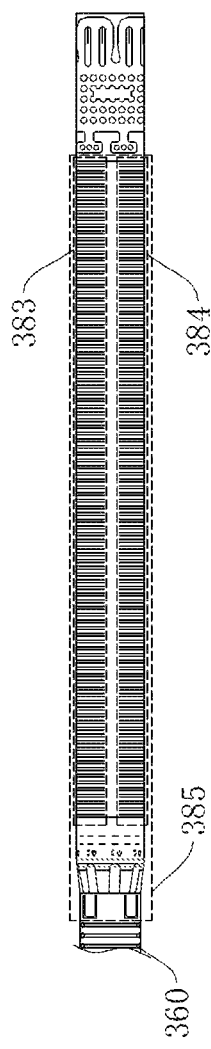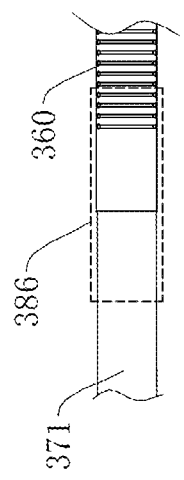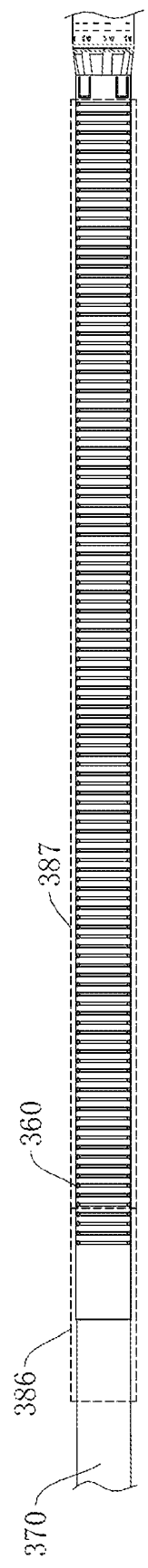
FIG. 32
FIG. 33
FIG. 34

SHEATH FOR DELIVERING INTERVENTIONAL INSTRUMENT AND SHEATH ASSEMBLY

TECHNICAL FIELD

The present invention relates to the technical field of medical devices, and in particular to a sheath for delivering an interventional instrument and a sheath assembly.

BACKGROUND

An interventional instrument delivery system generally includes a core assembly and a sheath slidably mounted around an outer periphery of the core assembly, and the two together constitute a sheath assembly, having a distal end able to enter the vascular system of a human and a proximal end connected to an operating handle. Considering the tortuous vascular system of a human being and the long distance that the sheath needs to travel, the direction of the distal end needs to be adjusted and controlled to move it to a target position. This raises more mechanical performance requirements for the sheath, for example, the axial support performance and bending compliance, etc. In addition, the position for exerting a force and the way of applying the force upon bending adjustment also affects the safety and the facility of the control of the operation to a certain extent.

SUMMARY

The present application provides a sheath for delivering an interventional instrument and a sheath assembly, the overall performance of which is improved by providing multiple layers and sections of the sheath, and improving, for example, the structure of a distal portion.

The present application provides a sheath for delivering an interventional instrument, which includes a distal end as a loading section for accommodating the interventional instrument, wherein the loading section has a multi-layer structure and comprises, from inside to outside, an inner lining tube, a metal tube and an outer wrapping membrane in sequence, wherein the metal tube comprises, from a proximal end to a distal end, a main tube and a head tube that are connected end-to-end; and the head tube comprises a body section, a plurality of elastic expansion pieces arranged circumferentially in intervals on the body section at a distal side thereof, and a first connector at a proximal side of the body section, wherein a distal side of the main tube is provided with a second connector, and the first connector and the second connector are fitted with each other through form-fitting.

Several alternative implementations are provided below; however, they are not intended to add additional limitation to the general solution, but are merely further supplemental or preferred implementations. Each alternative implementation can be combined with the main solution, and any alternative implementations can be combined.

Optionally, each expansion piece has a hollow area.

Optionally, the expansion pieces are evenly arranged in a circumferential manner, and 3 to 6 expansion pieces may be provided.

Optionally, the first connector is T-shaped.

Optionally, the body section forms an imaging area in a hollow area, where imaging points are provided.

Optionally, through holes are provided on both the body section and the first connector, and the inner lining tube and the outer wrapping membrane are heat melted to each other at the through holes.

Optionally, the hollow area comprises a plurality of through holes arranged in intervals in an axial direction of the sheath, and the total area of the through holes on each expansion piece is less than 50% of the area of the respective expansion piece.

Optionally, within the same expansion piece, the through hole has a larger area closer to the distal end.

Optionally, the through hole is circular or elliptical, and 2 to 5 through holes are provided on the same expansion piece.

Optionally, the hollow area includes at least one elongated hole, and the elongated hole extends along an axial direction of the head tube.

Optionally, two elongated holes are provided on the same expansion piece.

Optionally, the elongated hole extends with a consistent width.

Optionally, both ends of the elongated hole in the longitudinal direction have arc-shaped contours.

Optionally, there is an opening between two adjacent expansion pieces, each expansion piece has a narrowed portion at a proximal portion thereof, and the opening has a widened portion at a proximal portion thereof corresponding to the narrowed portion.

Optionally, the contour of the widened portion is smoothly curved.

Optionally, a middle portion the opening in a longitudinal direction thereof has a consistent width; and the consistent width of the opening is substantially equal to the width of the elongated hole.

Optionally, the width of the equal-width extension of the opening is approximately the same as the width of the elongated hole.

Optionally, a proximal end of the elongated hole extends beyond the narrowed portion of the expansion piece.

Optionally, the proximal end of the elongated hole extends beyond the narrowed portion of the expansion piece by 1 to 5 mm.

Optionally, a distal end of the expansion piece has a smooth outer edge.

Optionally, the metal tube includes, from a distal end to a proximal end, a head tube, a main tube, and an extension tube connected end-to-end in sequence, wherein the head tube and the main tube are both distributed in the loading section in the axial direction, and the extension tube is distributed in a bendable section.

Optionally, the extension tube is a hypotube.

Optionally, the head tube is formed by cutting a nickel-titanium alloy tube, and the main tube and the extension tube each are formed by cutting a stainless steel tube.

Optionally, the head tube is made of Nitinol, and each expansion piece has a converged configuration extending in the axial direction of the sheath and a flared configuration away from each other.

Optionally, the head tube and the main tube are connected to each other by connectors through form-fitting, and the main tube and the extension tube are connected to each other by hooking.

Optionally, two hollow areas are provided on the wall of the main tube, and two guide ribs are provided between the two hollow areas, which extend axially and are arranged opposite to each other.

Optionally, along the axial direction of the sheath, the outer wrapping membrane includes multiple sections, and the sections are made of different materials, or at least two of them are made of a same material.

Optionally, the strength of the outer wrapping membrane corresponding to the main tube is greater than the strength of the outer wrapping membrane corresponding to the distal end of the head tube.

Optionally, the main tube and the head tube are formed by cutting metal tubes of different materials.

The present application also provides a sheath assembly, which includes a sheath and a core assembly that are slidably nested within each other, and the core assembly includes a core tube with a distal portion mounted with a locking member for connecting an interventional instrument. The sheath is mounted around the outer periphery of the core assembly and is the sheath that is used for delivering an interventional instrument according to the present application.

Optionally, the core assembly further includes a bendable adjustable tube mounted around an outer periphery of the core tube; and the distal ends of the bendable adjustable tube and the core tube are fixedly connected to each other, and the proximal ends of the bendable adjustable tube and the core tube are slidable relative to each other.

Optionally, the core assembly further includes a bendable adjustable tube inside the core tube; and the distal ends of the bendable adjustable tube and the core tube are fixedly connected to each other, and the proximal ends are slidable relative to each other.

Optionally, the core tube extends distally out of the locking member, with a guide head fixed at the most distal end thereof. A loading position for an interventional instrument is formed between the guide head and the locking member; the interventional instrument in a compressed state is connected to the locking member at the loading position.

Optionally, the core tube comprises a compliant section adjacent to the locking member and a third extension section connected end-to-end to the compliant section and extending proximally, wherein the compliant section is a hypotube with a length ranging from 120 to 180 mm, and the third extension section is a wire casing or a hypotube.

Optionally, the bendable adjustable tube comprises, in sequence from a distal end to a proximal end, a pulling section and a second extension section, wherein the pulling section is a single piece and is a hypotube.

Optionally, the pulling section includes, from a distal end to a proximal end, a first pulling section, a transition section and a second pulling section, in which the first pulling section has higher flexibility than the second pulling section, and a ratio of a length of the first pulling section to a length of the compliant section is 1:0.7 to 1.5.

Optionally, the compliant section forms an axially extending first reinforcing rib extending axially by cutting.

Optionally, a width of a cut slit in the compliant section ranges from 0.1 to 1 mm, and a slit spacing ranges from 0.1 to 1 mm Optionally, in the compliant section, after bending, the extreme radius of curvature is smaller closer to the distal end.

Optionally, the slit width in the compliant section varies gradually, and becomes increasingly larger as the slit approaches the distal end.

Optionally, in the compliant section, the slit spacing gradually varies, and becomes increasingly smaller as the slit approaches the distal end.

Optionally, in the compliant section, the rigidity gradually changes, and becomes increasingly smaller as it approaches the distal end.

Optionally, the first pulling section forms an axially extending second reinforcing rib by cutting, and a circumferential position of the second reinforcing rib is offset from a circumferential position of the first reinforcing rib by 180 degrees.

Optionally, a width of a cut slit in the first pulling section ranges from 0.03 to 0.5 mm, and a slit spacing ranges from 0.2 to 0.85 mm.

Optionally, the second pulling section forms two axially extending third reinforcing ribs by cutting, and the two third reinforcing ribs are radially opposite to each other, and at circumferential positions that both are offset from the circumferential position of the first reinforcing rib by 90 degrees.

Optionally, in the second pulling section, a width of a cut slit ranges from 0.03 to 0.5 mm, and a slit spacing ranges from 0.2 to 0.85 mm.

Optionally, the transition section has an uncut structure that is a complete ring in the circumferential direction.

Optionally, the sheath includes, in sequence from a distal end to a proximal end, a loading section, a bendable section, and a first extension section in an axial direction, wherein a proximal end of an inner lining tube is connected to an inner sheath end-to-end, and the inner sheath is axially distributed in the bendable section and the first extension section; a proximal end of a main tube is connected to an extension tube made of a metal material, and the extension tube is axially distributed in the bendable section; and an outer wrapping membrane extends proximally and wraps around an outer periphery of the extension tube.

Optionally, the inner sheath has a multi-layer structure, with two fourth reinforcing ribs extending axially provided in an interlayer, wherein one of the fourth reinforcing ribs is at the same circumferential position as the first reinforcing rib, and the other of the fourth reinforcing ribs is at a circumferential position offset from the circumferential position of the first reinforcing rib by 180 degrees.

Optionally, the distal ends of the fourth reinforcing ribs extend to the proximal end of the extension tube or the distal end of the extension tube.

Optionally, the extension tube includes at least one fifth reinforcing rib extending axially, wherein one fifth reinforcing rib is provided, and is at the same circumferential position as the first reinforcing rib; or two fifth reinforcing ribs are provided, one of the fifth reinforcing ribs is at the same circumferential position as the first reinforcing rib, and the other of the fifth reinforcing ribs is at a circumferential position offset from the circumferential position of the first reinforcing rib by 180 degrees.

The present application also provides a method for processing a sheath, which includes:

Step S100: providing an inner sheath and forming a flared portion at a distal end of the inner sheath;

Step S200: mounting and fixing an inner lining tube around the outer periphery of the flared portion;

Step S300: mounting a metal tube around an outer periphery of a distal portion of the inner sheath and an outer periphery of the inner lining tube; and Step S400: wrapping an outer surface of the metal tube segmentally with an outer wrapping material, to form an outer wrapping membrane after the outer wrapping material in each section is heat melted.

The sheath may be the sheath according to the present application. The present application also provides a method for processing a sheath, which includes:

Step S100: forming a flared portion at a distal end of an inner sheath;

Step S200: mounting and fixing an inner lining tube on an outer periphery of the flared portion;

Step S300: mounting a metal tube around an outer periphery of the inner sheath and the inner lining tube; and Step S400: wrapping the outer surface of the metal tube segmentally with an outer wrapping material, to form an outer wrapping membrane after the outer wrapping material in each section is heat melted.

Optionally, in Step S200, a proximal end of the inner lining tube is provided with a plurality of ears arranged at intervals along the circumferential direction, and the plurality of ears are arranged around the outer periphery of the flared portion, and then the plurality of ears is wrapped with a fixing sleeve and fixed by heat melting.

Optionally, 3 to 6 ears are provided with are evenly arranged in a circumferential manner.

Optionally, the inner lining tube is made of PTFE.

Optionally, the fixing sleeve is made of Pebax.

Optionally, Step S400 specifically includes the following steps.

Step S410: wrapping a first connecting sleeve around the joint portion of the main tube and the head tube, wrapping a head sleeve around the head tube, and fixing the first connecting sleeve and the head sleeve by heat melting;

Step S420: wrapping a main sleeve around the outer periphery of the main tube and fixing it by heat melting;

Step S430: wrapping a second connecting sleeve around the proximal end of the extension tube and the inner sheath adjacent thereto and fixing it by heat melting; and Step S440: wrapping a connecting sleeve around the outer periphery of the extension tube and fixing it by heat melting.

Optionally, the main tube has hollow areas spaced apart, with a guide rib formed between adjacent hollow areas. Before the main sleeve is wrapped around the main tube, Step S420 further includes placing a lining on each hollow area and fixing it by heat melting.

Optionally, the lining is made of Pebax.

Optionally, the head sleeve and the connecting sleeve are made of TPU.

Optionally, the first connecting sleeve, the second connecting sleeve and the main sleeve are all made of Pebax.

The present application also provides an interventional instrument delivery system, which has opposite distal and proximal ends. The delivery system includes an operating handle at the proximal end and a sheath assembly connected to the operating handle and extending distally. The sheath assembly includes a sheath, and a core assembly, wherein the core assembly and the proximal end of the sheath both extend to, and are connected to, the operating handle.

At least one of the operating handle, the sheath, and core assembly in the delivery system may be the operating handles, sheaths, and core assemblies as described in the present application.

The present application also provides a method for delivering an interventional instrument, which includes loading the interventional instrument in a delivery system and then delivering it distally.

The delivery system includes an operating handle at a proximal end and a sheath assembly connected to the operating handle and extending distally. The sheath assembly includes a sheath and a core assembly, wherein the interventional instrument is connected to the core assembly and is enclosed by the sheath. The core assembly includes a core tube, a locking member fixed at a distal end of the core tube for connecting the interventional instrument, and a bendable adjustable tube. The distal ends of the bendable adjustable tube and the core tube are fixedly connected to each other, and the proximal ends of the bendable adjustable tube and the core tube are slidable relative to each other, and both extend to and are connected to the operating handle.

During the delivery process, the proximal end of the bendable adjustable tube is pulled to allow the proximal ends of the bendable adjustable tube and the core tube to slide relative to each other, and thus drive the distal end of the core tube to change its orientation to adapt to the delivery path.

The present application also provides an operating handle for delivering an interventional instrument into a human body. The operating handle is used to connect proximal ends of three tubes nested sequentially from an inside to an outside, and drives the proximal ends of the three tubes to move relative to each other. The three tubes are respectively a core tube, a bendable adjustable tube and a sheath from the inside to the outside. The operating handle includes a control component, a bending adjustment component and a front handle.

The control component includes:
a first support fixed relative to the front handle;
a first connecting member slidably mounted to the first support, wherein the proximal end of the sheath is fixed to the first connecting member; and
a first driving member movably mounted to the first support and driving the first connecting member to slide.

The bending adjustment component includes:
a second support fixed relative to the first support;
a second connecting member slidably mounted to the second support, wherein the proximal end of the bendable adjustable tube extends out of the sheath and is then fixed to the second connecting member;
a second driving member movably mounted to the second support and driving the second connecting member to slide; and
a tube fitting fixedly mounted at a proximal end of the second support, wherein the proximal end of the core tube extends out of the bendable adjustable tube and is then fixed to the tube fitting.

Optionally, a catheter is provided which is mounted around the sheath and connected to the front handle.

Optionally, the first driving member is rotatably mounted around the outer periphery of the first support, and a limiting mechanism for restraining the rotation angle of the first driving member is provided between the front handle and the first driving member.

Optionally, the limiting mechanism includes:
a sliding key, mounted in one of the front handle and the first driving member; and
an eyelet, provided in the other one of the front handle and the first driving member.

Optionally, an outer wall of the front handle is provided with a sliding chute. The sliding key is mounted in the sliding chute, and the eyelet is provided in an axial end surface of the first driving member.

Optionally, the limiting mechanism includes a locking pin that is screwed on the first driving member and abuts against the first support.

Optionally, the first support is cylindrical, the side wall of the first support is provided with a guide slot extending axially, the first connecting member is slidably mounted inside the first support, the first connecting member is provided with a guide key extending radially out of the guide slot, and the inner wall of the first driving member has a screw thread fitting with the guide key.

Optionally, the second support is cylindrical and arranged coaxially with the first support, and the second support and the first support are formed as one piece or separate pieces fixed together.

Optionally, the second driving member is rotatably mounted relative to the second support. The second support is provided with an operating port; and a portion of the second driving member is positioned inside the second support, and another portion of the second driving member is exposed from the operating port as a force applying portion. The second connecting member is located inside the second support and moves in association with the second driving member.

Optionally, the second driving member has internal screw threads, and at least a part of the second connecting member has external screw threads and extends into the second driving member. The second driving member drives the second connecting member to slide by threaded engagement.

Optionally, an inner wall of the second support is provided with a guide bar extending axially, at least a part of the second connecting member is located in the second support, and an outer wall of this part is provided with a guide groove corresponding to the guide bar.

In the delivery system of the present application, the operating handle, the core assembly, the sheath, and combinations therebetween are further developed, to better facilitate the bending adjustment and meet the performance requirements of each component.

BRIEF DESCRIPTION OF THE DRAWINGS

FIG. 1 is a schematic structural view of a delivery system according to the present application;

FIG. 2 is an exploded view of the delivery system in FIG. 1;

FIG. 5c is a schematic structural view of a core tube component according to an embodiment of the present application;

FIG. 6 is a schematic structural view of a bendable adjustable tube according to an embodiment of the present application;

FIG. 7 is a schematic structural view of a core tube at the compliant section;

FIG. 8 is a schematic structural view of another aspect of the core tube at the compliant section in FIG. 7;

FIG. 9 is a schematic structural view of a bendable adjustable tube according to an embodiment of the present application;

FIG. 10 is a schematic structural view of another aspect of the bendable adjustable tube in FIG. 9;

FIG. 11 is a deployed view of the bendable adjustable tube in FIG. 9;

FIG. 12 is a schematic structural view of a sheath according to an embodiment of the present application;

FIG. 18 is a schematic view showing each component in a sheath;

FIG. 19a is a schematic structural view of a head tube;

FIG. 19b is a deployed schematic structural view of a head tube according to another embodiment;

FIG. 20 is a schematic view of a distal end portion of a delivery system according to the present application;

FIGS. 25 to 34 are schematic diagrams showing components and related changes involved in a sheath processing process according to an embodiment of the present application;

Figure 3A:
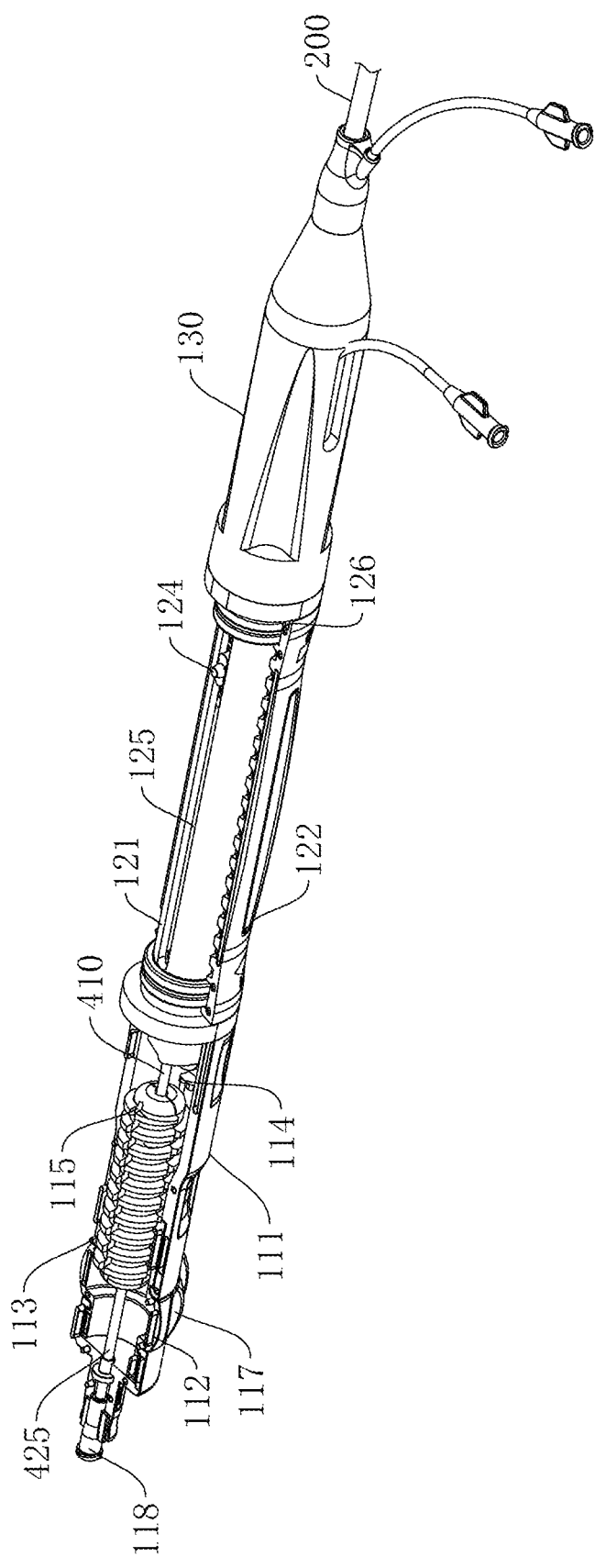
FIG. 3a is a schematic view showing an internal structure of an operating handle in FIG. 1.

LIST OF REFERENCE NUMERALS 100. operating handle;
110. bending adjustment component; 111. second support; 112. second driving member;
113. second connecting member; 114. guide bar; 115. guide groove; 116. operating port;
117. force applying portion; 118. Luer fitting;
120. control component; 121. first support; 122. first driving member; 123. first connecting member; 124. guide key; 125. guide slot; 126. eyelet;
130. front handle; 131. sliding key; 132. sliding chute;
200. catheter;
300. sheath; 310. loading section; 320. bendable section; 330. first extension section;

340. head tube; 341. opening; 342. imaging area; 343. first connector; 344. expansion piece; 345. hollow area; 346. body section; 347. through hole; 348. narrowed portion; 349. proximal end of elongated hole;
350. main tube; 351. second connector; 352. converged port; 353. hollow area; 354. hollow area; 355. guide rib;
360. extension tube; 3601. reinforcing rib (fifth reinforcing rib); 3602. reinforcing rib (fifth reinforcing rib);
370. inner sheath; 370A. distal portion; 370B. proximal portion; 3701. PTFE inner layer;
3702. woven layer; 3703. reinforcing rib (fourth reinforcing rib); 3704. woven layer; 3705. outer layer; 371. distal end; 372. core rod; 373. truncated cone section; 374. flared portion; 375. inner lining tube; 376. cut area; 377. fixing sleeve;
380. outer wrapping membrane; 381. first connecting sleeve; 382. head sleeve; 383. first lining; 384. second lining; 385. main sleeve; 386. second connecting sleeve; 387. connecting sleeve;
400. core assembly;
410. bendable adjustable tube; 411. first pulling section; 4111. reinforcing rib (second reinforcing rib); 412. second pulling section; 4121. reinforcing rib (third reinforcing rib);
4122. reinforcing rib (third reinforcing rib); 413. second extension section; 414. transition section;
420. core tube component; 421. guide head; 422. locking member; 4221. eyelet; 4222. wire distribution disc; 4223. pull wire; 4224. latching rod; 4225. wire running sleeve; 423. pressing strip; 424. inner core; 425. core tube; 4251. compliant section; 4252. third extension section; 4253. reinforcing rib (first reinforcing rib);
500. interventional instrument; 501. connecting lug;
600. aortic valve

DESCRIPTION OF THE EMBODIMENTS

The technical solutions according to the embodiments of the present application will be described clearly and fully in combination with the accompanying drawings in the embodiments of the present application. Apparently, the embodiments described are merely some but not all of the embodiments of the present application. All other embodiments obtained by persons of ordinary skill in the art based on the embodiments of the present application without creative efforts shall fall within the scope claimed by the present application.

It should be noted that when a component is described to be "connected" to another component, it may be directly connected to another component or may be indirectly connected to another component through an intermediate component. When a component is "provided on" another component, it may be directly provided on another component or may be provided on another component through an intermediate component.

Unless otherwise defined, all technical and scientific terms used herein have the same meaning as commonly understood by persons skilled in the art. The terms used in the descriptions of the present application are for the purpose of describing specific embodiments only and are not intending to limit the present application. The term "and/or" as used herein includes any combinations of one or more of the listed options, as well as the combination of all of the listed options.

Referring to FIGS. 1 to 4, an embodiment of the present application provides a delivery system, which has opposite distal and proximal ends. The delivery system includes an operating handle 100 at the proximal end, and a sheath 300 and a core assembly 400 connected to the operating handle 100 and extending toward the distal end. The sheath 300 is slidably fitted to an outer periphery of the core assembly 400.

The core assembly includes a core tube, and a locking member fixed at a distal end of the core tube and used to connect an interventional instrument. The locking member may be in various forms, for example, a groove which is configured for connecting a connecting lug on a stent, a protrusion head that protrudes radially outwardly, or a wire-controllable means in which a long wire or wire loop is connected to the stent. Regardless what structure is used, the purpose is to establish the connection between it with the connecting lug on the stent.

In some embodiments, the core assembly further includes a bendable adjustable tube mounted around an outer periphery of the core tube. The distal ends of the bendable adjustable tube and the core tube are fixedly connected to each other, and their proximal ends extend to and are connected to the operating handle, and are slidable relative to each other.

In some embodiments, the core assembly further includes a bendable adjustable tube in the core tube. The distal ends of the bendable adjustable tube and the core tube are fixedly connected to each other, and their proximal ends extend to and are connected to the operating handle, and are slidable relative to each other.

Regardless of the radial-internal-external-relationship between the core tube and the bendable adjustable tube, relative movement of their proximal ends is required. Generally, upon bending adjustment, the position of the proximal end of the core tube is maintained fixed, or is taken as a reference, and the proximal end of the bendable adjustable tube is pulled. Different radial-internal-external-relationships between the core tube and the bendable adjustable tube cause the two to abut at different positions at a turning site. In the following embodiments and drawings, examples are given with the bendable adjustable tube located at the outside. The structure of the operating handle can be adapted correspondingly according to the radial-internal-external-relationship between the core tube and the bendable adjustable tube, so that their proximal ends can move relative to each other.

In other embodiments, the delivery system may further include a catheter 200 that is fixed relative to the operating handle 100. The catheter 200 serves to establish a channel to prevent injury to tissues in the body when the sheath 300 moves back and forth. The interventional instrument is loaded on the core assembly 400 and enclosed by the sheath 300, and then enters the body with the catheter 200. The sheath 300 can move axially relative to the interventional instrument and the core assembly 400 to release the interventional instrument and to be withdrawn when necessary.

The bending adjustment is mainly performed by controlling the operating handle 100. In an embodiment shown in FIGS. 3a and 4, the operating handle 100 is configured to connect the proximal ends of the three tubes which are sequentially nested within each other from the inside to the outside, and drive the proximal ends of the three tubes to move relative to each other. The three tubes are respectively, from the inside to the outside, the core tube, the bendable adjustable tube and the sheath. The operating handle 100 includes a control component 120, a bending adjustment component 110 and a front handle 130.

The control component 120 includes:
a first support 121 fixed relative to the front handle 130;

a first connecting member 123 slidably mounted to the first support 121, wherein the proximal end of the sheath is fixed to the first connecting member 123; and a first driving member 122 movably mounted to the first support 121 and configured for driving the first connecting member 123 to slide.

The bending adjustment component 110 includes:

a second support 111 fixed relative to the first support 121;

a second connecting member 113 slidably mounted to the second support 111, wherein the proximal end of the bendable adjustable tube extends out of the sheath and is then fixed to the second connecting member 113;

a second driving member 112 movably mounted to the second support 111 and configured for driving the second connecting member 113 to slide; and a tube fitting fixedly mounted at a proximal end of the second support 111, wherein the proximal end of the core tube extends out of the bendable adjustable tube and is then fixed to the tube fitting.

Specifically, the control assembly 120 includes the first support 121. The first driving member 122 is rotatably mounted around the outer periphery of the first support 121. A side wall of the first support 121 is provided with a guide slot 125 extending in the axial direction. The first connecting member 123 is slidably mounted inside the first support 121, and the first connecting member 123 is provided with a guide key 124 extending out of the guide slot 125. An inner wall of the first driving member 122 has a screw thread for engaging with the guide key 124.

As for the configuration of the first support 121, according to one embodiment, the first support 121 is cylindrical, the side wall of the first support 121 is provided with the guide slot 125 extending in the axial direction, and the first connecting member 123 is slidably mounted inside the first support 121. The first connecting member 123 is provided with the guide key 124 extending radially out of the guide slot 125, and the inner wall of the first driving member 122 has a thread engaging with the guide key 124.

Figure 4:
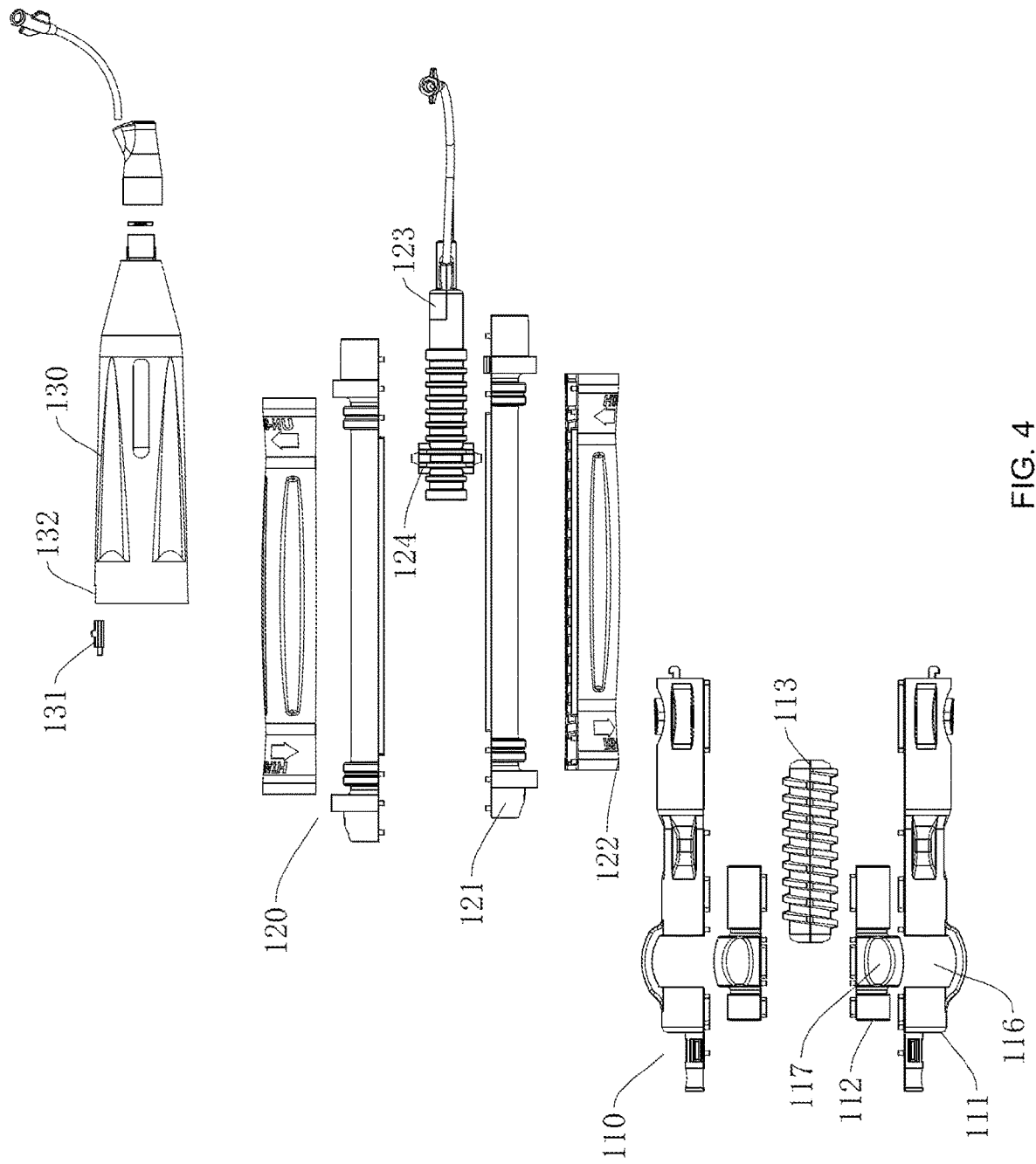
FIG. 4 is an exploded view of the operating handle in FIG. 1.

Specifically, the first support 121 is substantially cylindrical, and may be configured as one single piece, or has a plurality of separate pieces radially snap-fit with each other (as shown in FIG. 4). When the first driving member 122 rotates, the first connecting member 123 is driven by the guide key 124 to slide inside the first support 121. Due to the restriction by the guide slot 125, the first connecting member 123 only moves axially without rotation.

The front handle 130 is fixedly connected to the first support 121, and the proximal end of the catheter 200 is fixedly inserted in the front handle 130. The proximal end of the sheath 300 is fixedly mounted to the first connecting member 123, and the sheath 300 extends distally through the catheter 200.

As for the mating relationship between the first support 121 and the second support 111, according to one embodiment, the second support 111 is cylindrical and arranged coaxially with the first support 121. The second support 111 and the first support 121 may be formed as one single piece or as separate pieces which are fixed together.

For the mating relationship between the second driving member 112 and the second support 111, according to one embodiment, the second driving member 112 is rotatably mounted relative to the second support 111. The second support 111 is provided with an operating port 116; and a portion of the second driving member 112 is positioned inside the second support 111, and at least another portion of the second driving member 112 is exposed from the operating port 116 to serve as a force applying portion 117. The second connecting member 113 is located inside the second support 111 and moves in association with the second driving member 112.

Specifically, the bending adjustment component 110 includes the second support 111, which is substantially cylindrical and fixed relative to the first support 121. The second support 111 may be formed as one single piece or may have separate pieces which are radially snap-fitted (as shown in FIG. 4). The second support 111 and the first support 121 are formed as separate elements which are coaxially arranged and connected end-to-end.

Correspondingly, the bending adjustment component 110 further includes the second driving member 112. For the specific configuration of the second driving member 112, according to an embodiment, the second driving member 112 has internal screw threads, and at least a portion of the second connecting member 113 is provided with external screw threads and extends into the second driving member 112. As a result, the second driving member 112 can drive the second connecting member 113 to slide with the threaded connection.

Specifically, the second driving member 112 is rotatably mounted relative to the second support 111. The second support 111 is partially provided with the operating port 116; and a portion of the second driving member 112 is positioned inside the second support 111, and at least another portion of the second driving member 112 is exposed from the operating port 116 and serves as the force applying portion 117. The second driving member 112 is substantially cylindrical and has internal screw threads, and the second connecting member 113 is slidably mounted in the second driving member 112.

To restrain the movement of the second connecting member 113, according to one embodiment, an inner wall of the second support 111 is provided with a guide bar 114 extending in the axial direction, at least a portion of the second connecting member 113 is located in the second support 111, and an outer wall of this portion is provided with a guide groove 115 corresponding to the guide bar 114. In this embodiment, the guide bar 114 is retained in the guide groove 115 such that the second connecting member 113 can only slide axially relative to the second support 111.

It is understandable from the above descriptions that the bending adjustment of the operating handle 100 is mainly achieved by the rotation of the respective components. In order to prevent unstable bending adjustment caused by the relative movement of each component during the operation, a limiting mechanism may be provided. According to an embodiment, the first driving member 122 is rotatably mounted around the outer periphery of the first support 121, and a limiting mechanism for restraining the rotation angle of the first driving member 122 is provided between the front handle 130 and the first driving member 122.

Accordingly, this embodiment exemplarily provides one form of the limiting mechanism. In this embodiment, the limiting mechanism includes: a sliding key 131 mounted in one of the front handle 130 and the first driving member 122; and an eyelet 126, provided in the other one of the front handle 130 and the first driving member 122.

When the sliding key 131 is engaged with the eyelet 126, the positions of the front handle 130 and the first driving member 122 in the circumferential direction are determined. Therefore, the axial position of the first connecting member 123 relative to the front handle 130 is determined, and the bending adjustment function of the operating handle 100 is locked, ensuring the stability during use. In one specific embodiment, an outer wall of the front handle 130 is provided with a sliding chute 132. The sliding key 131 is mounted in the sliding chute 132, and the eyelet 126 is provided in an axial end surface of the first driving member 122.

Figure 3C:
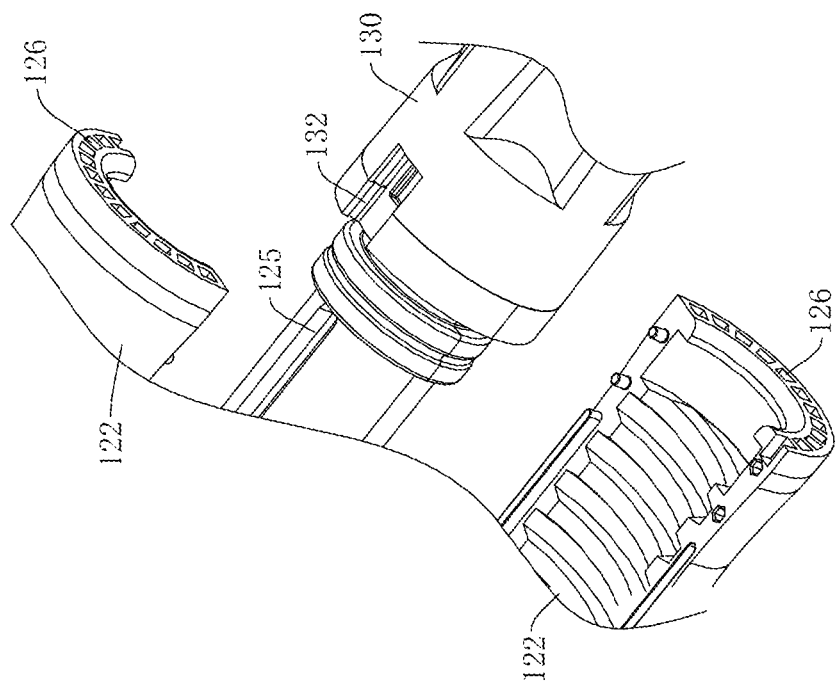
FIG. 3c is partially enlarged view of FIG. 3b.

It is possible to lock the first driving member 122 at multiple positions by increasing the number of the eyelets 126. Referring to FIG. 3c, a plurality of eyelets are provided in the axial end surface of the first driving member 122, which are arranged sequentially along the circumferential surface of the first driving member 122. The increase in the number of eyelets 126 can increase the locking positions of the first driving member 122. However, the increase in the number of eyelets 126 will increase the difficulty in manufacturing the first driving member 122 and reduce the distance between adjacent eyelets 126, thereby reducing the strength of individual eyelets 126. Therefore, the specific number can be adjusted according to the design requirements, practical working conditions, and actual product size.

Figure 3B:
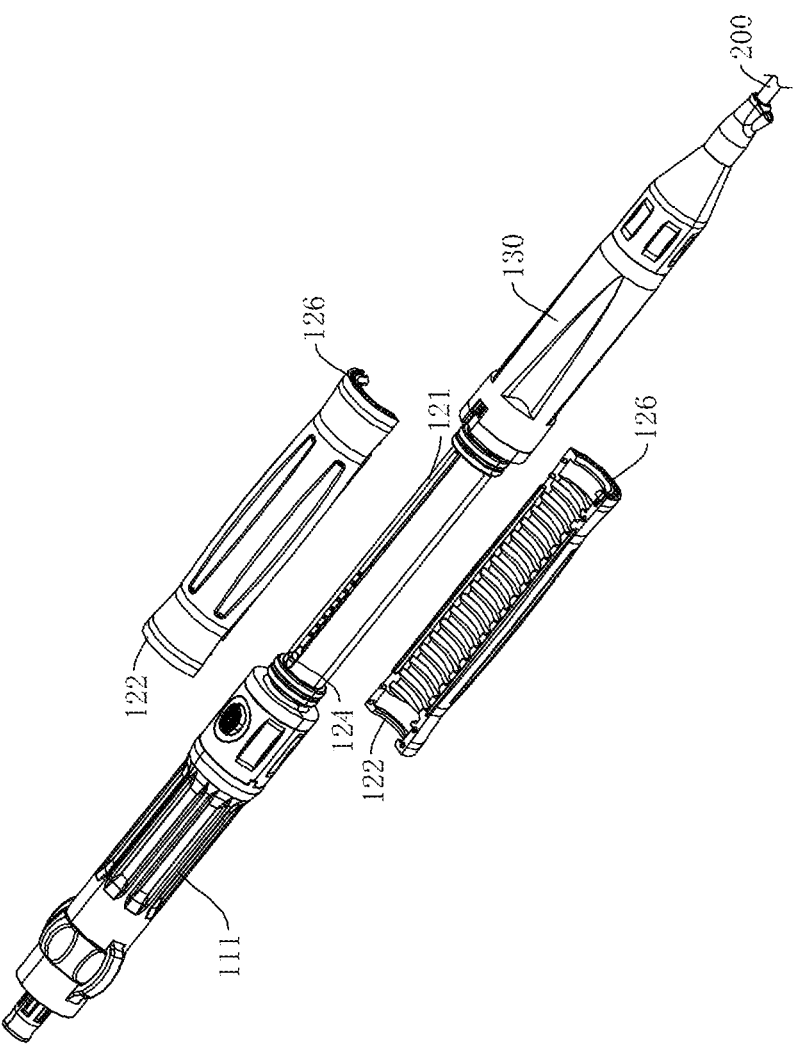
FIG. 3b is a schematic view showing another aspect of an internal structure of the operating handle in FIG. 1.

In the embodiments shown in FIGS. 3b and 3c, because the first driving member 122 includes separate upper piece and lower piece that are snap-fitted together, there are two options for the eyelet 126 near the separation face. In one option, the eyelet is opened toward the separation face, and in the other option, the eyelet is designed to avoid the separation face and has a closed form. Either one of the two options can be used for any specific product.

Correspondingly, a limiting mechanism may also be provided between the first driving member 122 and the first support 121 to achieve the above-mentioned functions. In one embodiment, the limiting mechanism includes a locking pin (not shown) that is screwed on the first driving member 122 and abuts against the first support 121. The locking pin is screwed to the first driving member 122, and thus the position of the locking pin relative to the first driving member 122 is determined, thereby achieving the positioning of the first support 121. When the relative positions of the first driving member 122 and the first support 121 are determined, the function of the above-mentioned limiting mechanism is achieved, and the locking principle will not be further described herein.

The present application provides a core assembly according to one embodiment for delivering an interventional instrument, which includes a core tube, a locking member fixed at a distal end of the core tube for connecting the interventional instrument, and a bendable adjustable tube mounted around an outer periphery of the core tube. The distal ends of the bendable adjustable tube and the core tube are fixedly connected to each other, and the proximal ends of the bendable adjustable tube and the core tube can slide relative to each other. The core assembly 400 includes the bendable adjustable tube 410 and a core tube 425 nested in one another. The bendable adjustable tube 410 surrounds the outside of the core tube 425, with their distal ends fixedly connected to each other, and their proximal ends can slide relative to each other. The proximal end of the bendable adjustable tube 410 is fixed to the second connecting member 113, and the proximal end of the core tube 425 extends out of the second connecting member 113 and is then fixed to a tail, that is, the proximal end, of the second support 111. To facilitate the connection with an external tube, the proximal end of the core tube 425 is provided with a tube fitting, such as a Luer fitting 118.

When the interventional instrument needs to be released or withdrawn, the first driving member 122 is rotated to allow the first connecting part 123 to move axially, and drive the sheath 300 to move relative to the core assembly 400. When bending adjustment is required, the second driving member 112 is rotated to move the second connecting part 113 axially, and drive the proximal end of the bendable adjustable tube 410 to move relative to the proximal end of the core tube 425. Because the distal ends of the bendable adjustable tube 410 and the core tube 425 are fixed relative to each other, the relative movement of their proximal ends will cause their distal ends to deflect and curve radially together.

Referring to FIGS. 5a to 11, the core assembly 400 includes the bendable adjustable tube 410 and a core tube component 420. The core tube component 420 includes the core tube 425, and the locking member 422 is mounted at the distal end of the core tube 425 and configured to connect the interventional instrument. The bendable adjustable tube 410 is mounted around the outer periphery of the core tube 425. The distal ends of the bendable adjustable tube 410 and the core tube 425 are fixedly connected to each other, and the proximal ends of the bendable adjustable tube 410 and the core tube 425 can slide relative to each other.

The distal end of the bendable adjustable tube 410 extends to a position adjacent to a proximal end of the locking member 422. The bendable adjustable tube 410 may be directly fixed to the core tube 425 or the locking member 422 or both. The bendable adjustable tube 410 and the core tube 425 both may be made of metal materials such as hypotubes, and they can be fixed by welding, bonding or by a fastener.

The distal end of the core tube 425 further extends out of the locking member 422 and is fixed to a guide head 421. A distal end of the guide head 421 has a conical-shaped head to facilitate travel within the body. A position between the guide head 421 and the locking member 422 is configured as a loading position of the interventional instrument. The compressed interventional instrument is located at this position, fitted to and restrained by the locking member 422.

In one embodiment, the core tube 425 is provided with an inner core 424 extending therein. A distal end of the inner core 424 extends out of the locking member 422 and is fixed to the guide head 421. The extension length of a proximal end of the inner core 424 is not strictly limited. A position on the outer periphery of the inner core 424 between the guide head 421 and the locking member 422 is formed as the loading position of the interventional instrument. The compressed interventional instrument is located at this position and fitted to and restrained by the locking member 422. Since the core tube 425 does not extend to the loading position, and the inner core 424 has a smaller outer diameter compared with the core tube 425, so the radial space at the loading position is increased.

Figure 5B:
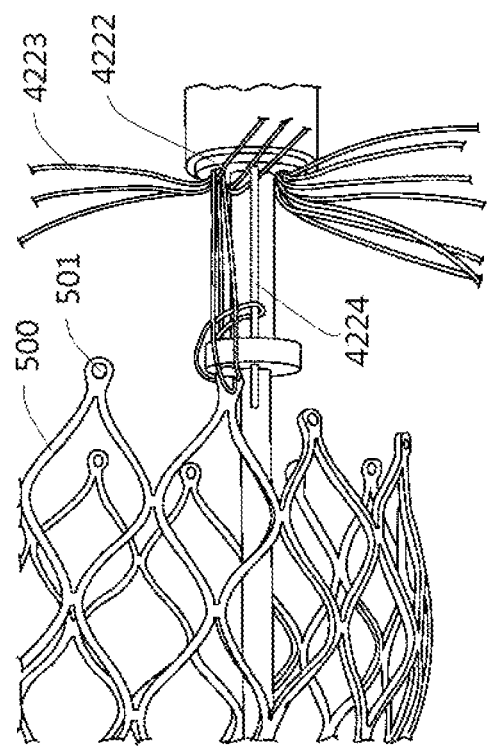
FIG. 5b is a schematic view showing the locking member in FIG. 5a fitted with an interventional instrument.
Figure 5A:
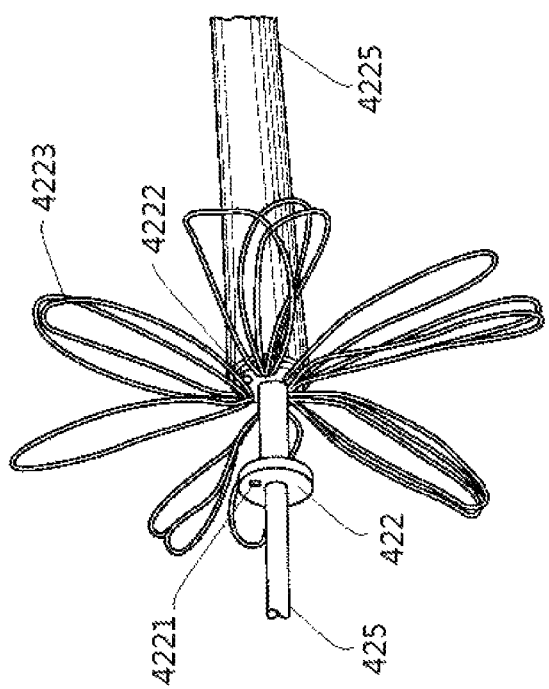
FIG. 5a is a schematic structural view showing a locking member of a core assembly adopting a wire control means according to an embodiment of the present application.

Referring to FIGS. 5a and 5b, in some embodiments, the locking member is a wire-controlled means. The proximal end of the interventional instrument 500 has a connecting lug 501. The connecting lug 501 generally has a hole or hook through which a pull wire 4223 extends. The locking member 422 has an eyelet 4221. A distal end of a latching rod 4224 is fitted with the eyelet 4221, and a proximal end of the latching rod 4224 may extend to the operating handle.

In a loaded state, the pull wire 4223 extends through the connecting lug 501 and then is connected to the locking rod 4224. Since the distal end of the locking rod 4224 is inserted into the eyelet 4221, the connecting lug 501 is restrained by the pull wire 4223 from releasing from the locking member 422. When the interventional instrument needs to be released, the locking rod 4224 is pulled toward the proximal end and then released from the eyelet 4221, and thus the pull wire 4223 is released, allowing the connecting lug 501 to disconnect from the locking member 422.

When a plurality of connecting lugs 501 are provided, a plurality of pull wires 4223 are provided correspondingly. The pull wires 4223 are respectively extended distally through a wire distribution disc 4222. To organize the pull wires, a wire running sleeve 4225 may be provided, which is mounted around the outer periphery of the core tube 425 with a passage formed therebetween through which the pull wires 4223 extend.

The engageable latching rod 4224 and eyelet 4221 together form a set of latching mechanisms. Multiple sets of latching mechanisms can be provided as required, which are arranged in sequence along the circumferential direction of the locking member 422.

Referring to FIG. 5c, in some embodiments, one or more limiting grooves are provided on the outer periphery of the locking member 422, and the interventional instrument has one or more connecting lugs inserted into the one or more limiting grooves. The limiting groove is configured for limiting the interventional instrument in the axial position, and only allows the interventional instrument to be released after radial expansion. To prevent the connecting lug from damaging the tissue due to any sudden outward turns when the connecting lug is accidentally disengaged, or during release, pressing strips 423 corresponding to respective limiting grooves are further fixedly provided at the locking member 422. After the interventional instrument is loaded, the pressing strips 423 which are restrained by the sheath restrict the connecting lugs into the limiting grooves, to further improve the safety. During release, the pressing strips 423 of the flexible materials deflects outwardly to allow the connecting lug to be disengaged from the locking member 422.

The inner core 424 and the core tube 425 are both tubular. There is no relative movement required for the core tube 425 and the inner core 424 in the axial direction, so they may be nested, and welded at one or more welding points. If necessary, a bushing may be provided at the welding position to fill the radial gap between them. The inner core 424 and the core tube 425 are welded to the bushing respectively. The bushing may be made of the same material as the core tube 425.

One end of the core tube 425 is directly or indirectly fixed to the proximal end of the locking member 422, and the other end of the core tube 425 extends towards the operating handle.

In one embodiment, to facilitate the bending adjustment, the core tube 425 includes a compliant section 4251 adjacent to the locking member 422, and a third extension section 4252 connected to the compliant section 4251 end-to-end and extending proximally therefrom. The compliant section has less rigidity than the third extension section, that is, it has a better flexibility and can be more easily bent.

In one embodiment, the compliant section 4251 is a hypotube or a spring tube (that is, a spirally extending reinforcing rib is provided in an interlayer of the tube wall). The length of the compliant section 4251 is in the range of 120 mm to 180 mm, for example, 150 mm.

The third extension section 4252 is a hypotube or a wire casing (which is woven or twisted with metal wires). The wire casing may be wrapped with a PTFE film which provides a lubricating function.

In other embodiments, the core tube 425 is entirely a hypotube. The hypotube can not only ensure the axial support but also be bent radially. To control the bending direction of the compliant section 4251, the compliant section 4251 can be provided with an axially extending reinforcing rib. The reinforcing rib is obtained by cutting a corresponding portion of the hypotube (where an uncut or less cut area is the reinforcing rib). The reinforcing rib may extend to the most proximal end of the core tube 425. However, since the core tube 425 has no obvious bending adjustment requirement at the position adjacent to the proximal end, the reinforcing rib can extend to the middle portion or a position just adjacent to the proximal end of the core tube 425.

Referring to FIGS. 7 and 8, when the compliant section 4251 is cut, the width of a cut slit 4254 (i.e. diameter of the laser spot) is 0.1 to 1 mm, and the slit spacing 4255 (i.e. the uncut portion left between adjacent two cut slits 4254) is 0.1 to 1 mm. An uncut portion extending along the axial direction serves as the reinforcing rib 4253.

In some embodiments, it is the core tube that is to be bent. The compliant section is configured such that the closer to the distal end, the smaller the extreme radius of curvature is after being bent. This makes the distal end of the core tube more adaptable to complex paths. Specifically, for the compliant section, at least one of the following features may be present.

The slit width in the compliant section changes gradually, and it becomes increasingly larger as it approaches the distal end.

In the compliant section, the slit spacing gradually changes, and it becomes increasingly smaller as it approaches the distal end.

In the compliant section, the rigidity (flexibility) gradually changes, and the rigidity becomes increasingly smaller as it approaches the distal end.

Referring to FIGS. 9 to 11, the bendable adjustable tube 410 is mounted around the core tube 425, and the bendable adjustable tube 410 includes, from the distal end to the proximal end, a pulling section and a second extension section 413 in sequence. The pulling section is in the form of a single piece, and it is a hypotube in this embodiment.

A distal end of the pulling section extends in proximity to the proximal end of the locking member 422 and is fixed to the core tube 425. To prevent the reverse positioning of the pulling section, a hole may be provided in the ends of the pulling section during processing to make different marks, to thereby identify the orientation of the distal and proximal ends during assembly.

The pulling section includes, from the distal end to the proximal end, a first pulling section 411, a transition section 414, and a second pulling section 412 in sequence.

In this application, the bendable adjustable tube 410 is located outside the core tube 425, that is, the force applying element is arranged outside and the passively bent object is arranged inside during bending adjustment. Such an arrangement achieves a larger bending angle compared with an arrangement where the force applying element is arranged inside and the passively bent object is arranged outside.

The first pulling section 411 is provided with a reinforcing rib 4111 by cutting, which is offset from the reinforcing rib 4253 of the compliant section 4251 in the circumferential direction by 180 degrees.

The second pulling section 412 is also cut. When the first pulling section 411 and the second pulling section 412 are cut, the width of the cut slits 4113 are respectively 0.03 mm to 0.5 mm, and the slit spacings 4114 are 0.2 mm to 0.85 mm. The first pulling section 411 is located at an expected bending position, and is relatively softer and more flexible. The second pulling section 412 is relatively hard. However, to ensure that the second pulling section has a certain degree of flexibility to be bent during packaging and transportation, and be bent according to the blood vessel after entering the human body during the operation, the second pulling section is cut and also has cut slits 4123 and slit spacings 4124. In practice, the slit widths and slit spacings in different sections can be adjusted according to the actual rigidity requirements.

The second pulling section 412 is cut to form reinforcing ribs 4121 and 4122. The two reinforcing ribs are radially opposite to each other. That is, the two reinforcing ribs are circumferentially offset by 180 degrees. The two reinforcing ribs are both circumferentially offset from the reinforcing rib 4111 of the first pulling section 411 by 90 degrees.

The transition section 414 is not cut. The transition section 414 connects the first pulling section 411 to the second pulling section 412, and bears the stress at different positions in the circumferential direction.

There is no particular bending requirement for the second extension section 413. It mainly serves to transmit the pulling force. For example, an uncut hypotube may be used, which extends proximally and is connected to the operating handle.

During the bending adjustment process, the first pulling section 411 and the compliant section 4251 are mainly bent to a greater degree. Therefore, when a hypotube is cut, a target bending angle greater than 270° is generally required. The first pulling section and the compliant section are respectively provided with a single reinforcing rib structure, which ensures that no stretch occurs during the bending adjustment. The first pulling section 411 and the compliant section 4251 which are aligned in the radial direction have a moderate flexibility, facilitating the bending adjustment while ensuring the force transmission. In general, the bendable adjustable tube 410 is 5 to 10 mm longer than the core tube 425, to compensate for axial offset after bending. The core tube 425 and the sheath 300 are passive elements during the bending adjustment, and the bendable adjustable tube 410 is the force applying element.

Figure 13:
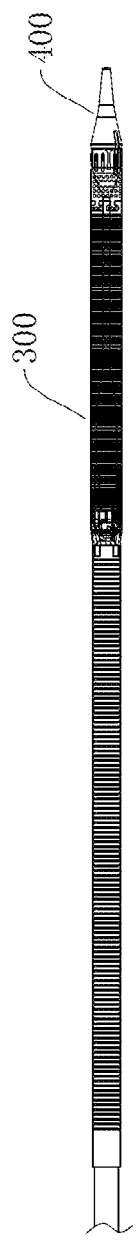
FIG. 13 is a schematic view showing the structure obtained after the components in FIG. 5c, FIG. 6, and FIG. 12 are assembled.

Referring to FIGS. 12 to 13, in order to adapt to the bending adjustment or adjust the orientation of the distal end adaptively when traveling in the body, the outermost sheath 300 has different flexibilities at different axial sections. The sheath 300 includes, from the distal end to the proximal end, a loading section 310, a bendable section 320, and a first extension section 330. During use, the bend mainly occurs at a position adjacent to the proximal end of the loading section which is configured for accommodating the interventional instrument 500, i.e., at the bendable section 320.

Figure 14:
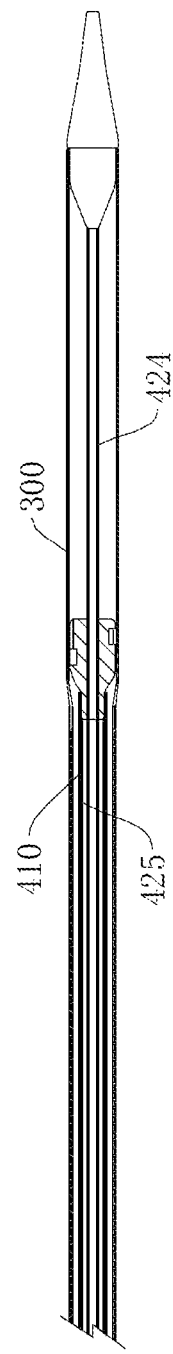
FIG. 14 is a cross-sectional view of a sheath assembly according to an embodiment of the present application.
Figure 15A:
FIG. 15a is a schematic structural view of the sheath assembly in FIG. 14 with an interventional instrument loaded therein.
Figure 15B:
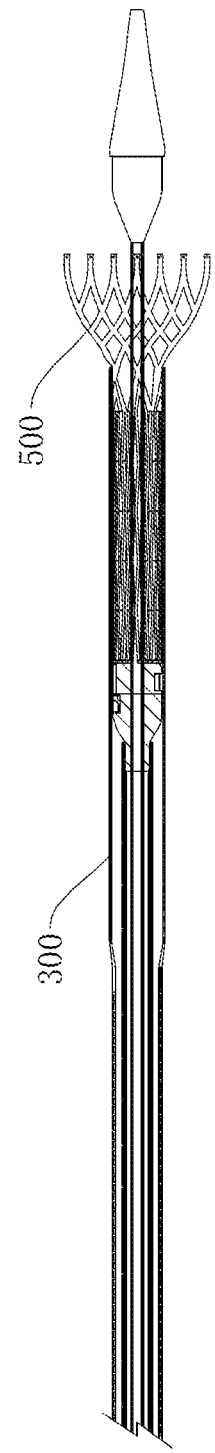
FIG. 15b is a schematic structural view showing the interventional instrument in FIG. 15a partially released.
Figure 15C:
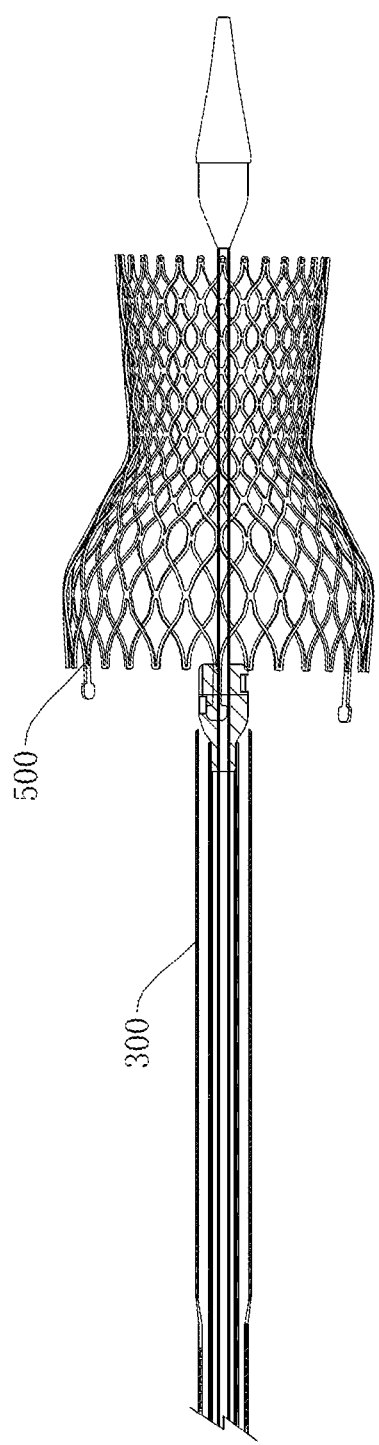
FIG. 15c is a schematic structural view showing the interventional instrument in FIG. 15a completely released.
Figure 15D:
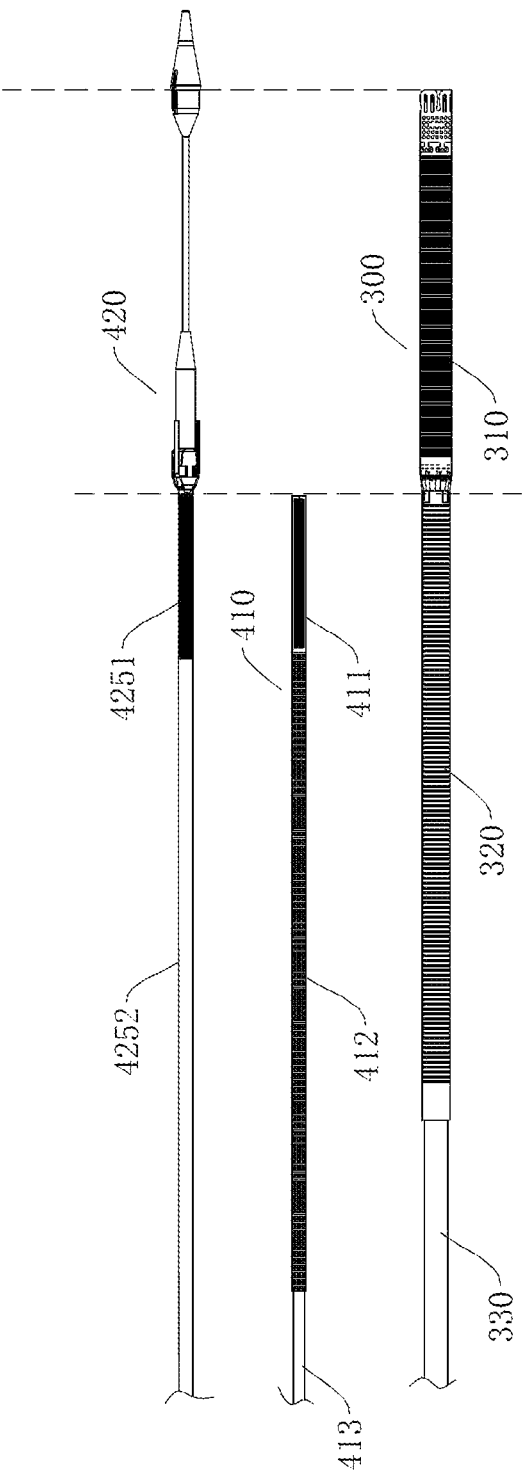
FIG. 15d is a schematic view illustrating the relationships between the axial sections of each tube according to an embodiment of the present application.

Referring to FIGS. 14 to 15d, according to one embodiment, the nesting relationship of the sheath 300, the core tube component 420, and the bendable adjustable tube 410, and the release process of the interventional instrument, are illustrated. FIG. 15d also illustrates the approximate axial positional relationships of various sections of the sheath 300, the core tube component 420, and the bendable adjustable tube 410. The sheath 300 has a multi-layer composite structure in each section. Specifically, for a certain section, a multi-layer structure is adopted which includes different parts during processing. The structure and the manufacturing process of the sheath 300 are also the improvements of this application.

Figure 16:
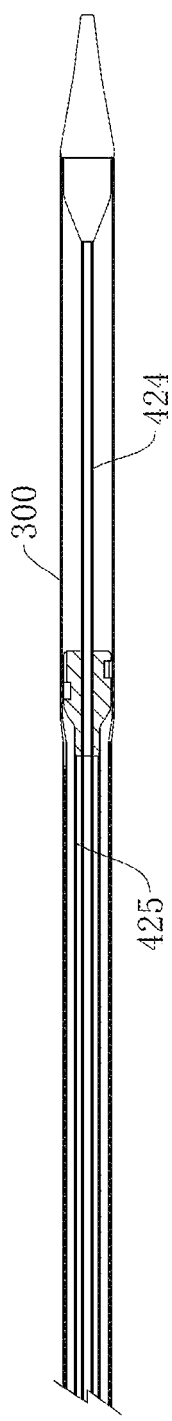
FIG. 16 is a cross-sectional view showing a sheath and a core tube component according to an embodiment of the present application.
Figure 17A:
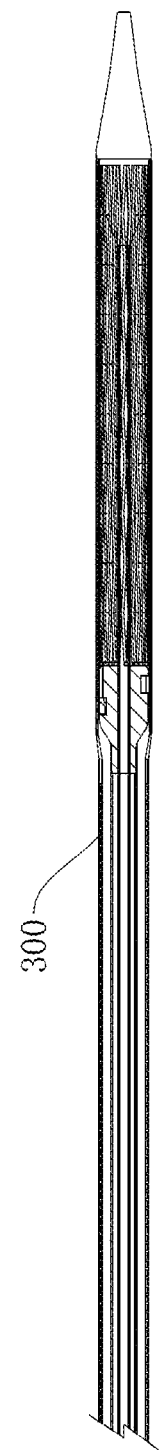
FIG. 17a is a schematic structural view of the structure in FIG. 16, wherein an interventional instrument is loaded.
Figure 17B:
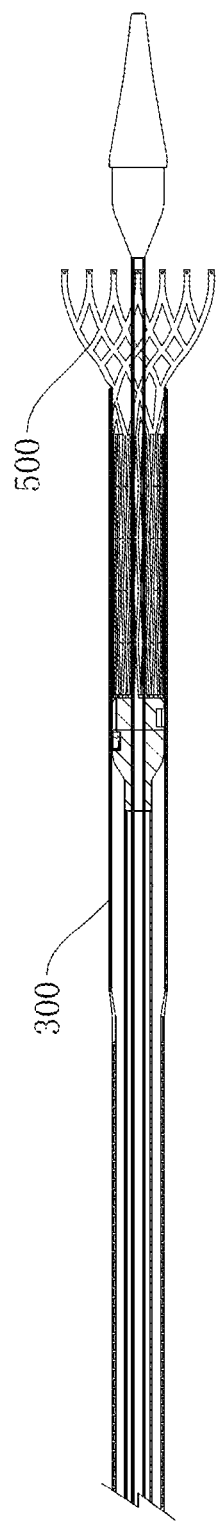
FIG. 17b is a schematic structural view showing the interventional instrument in FIG. 17a half-released.
Figure 17C:
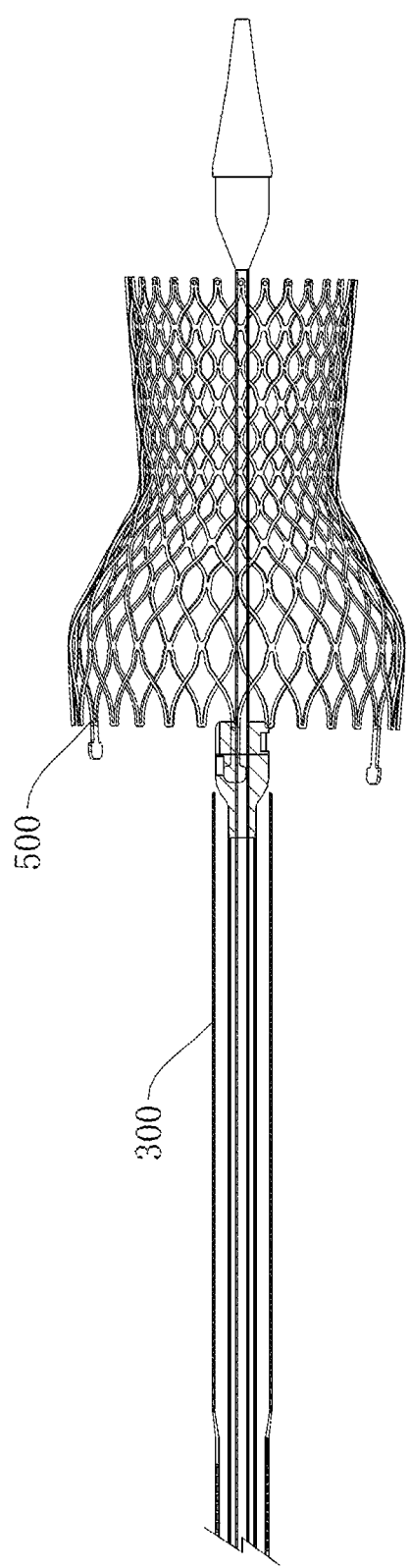
FIG. 17c is a schematic structural view showing the interventional instrument in FIG. 17a completely released.
Figure 17D:
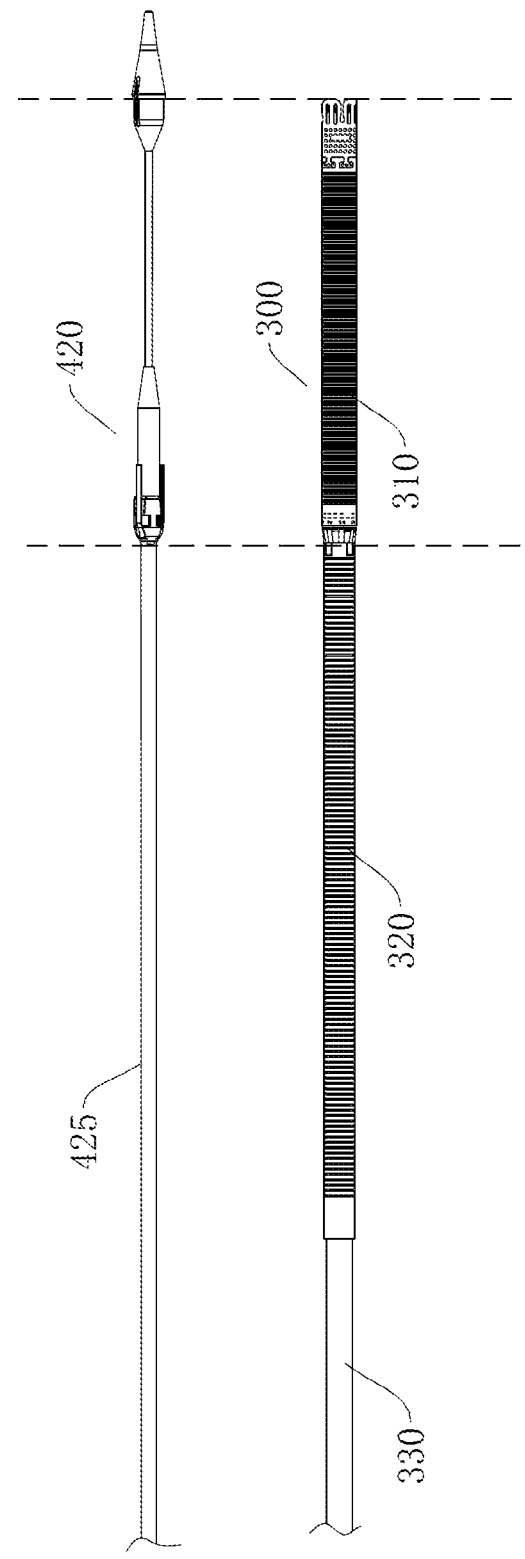
FIG. 17d is a schematic view showing the relative relations between the axial sections of each tube according to an embodiment of the present application.
Figure 23:
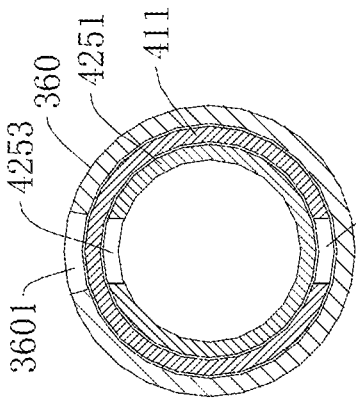
FIG. 23 is a cross-sectional view of FIG. 20 at position B-B.
Figure 22:
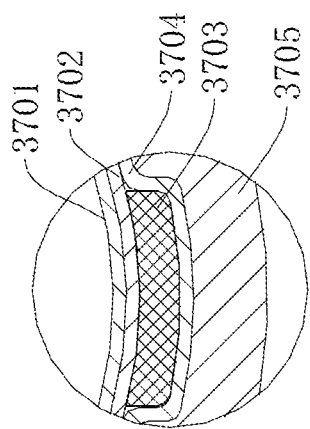
FIG. 22 is an enlarged view of area A in FIG. 21.
Figure 21:
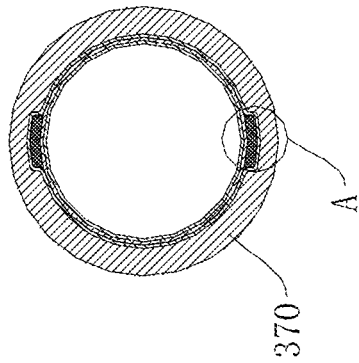
FIG. 21 is a cross-sectional view of an inner sheath in FIG. 20 at position C-C.
Figure 26:
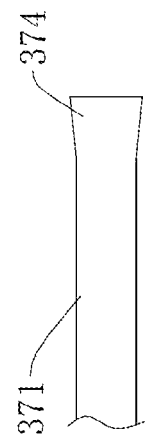
Figure 25:
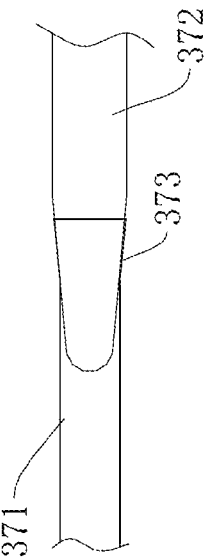
Figure 24:
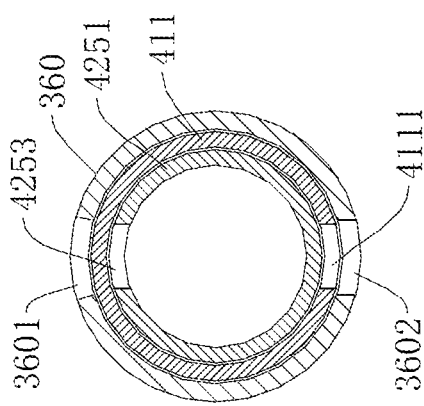
FIG. 24 is a cross-sectional view of FIG. 20 at position B-B according to another embodiment.
Figure 35:
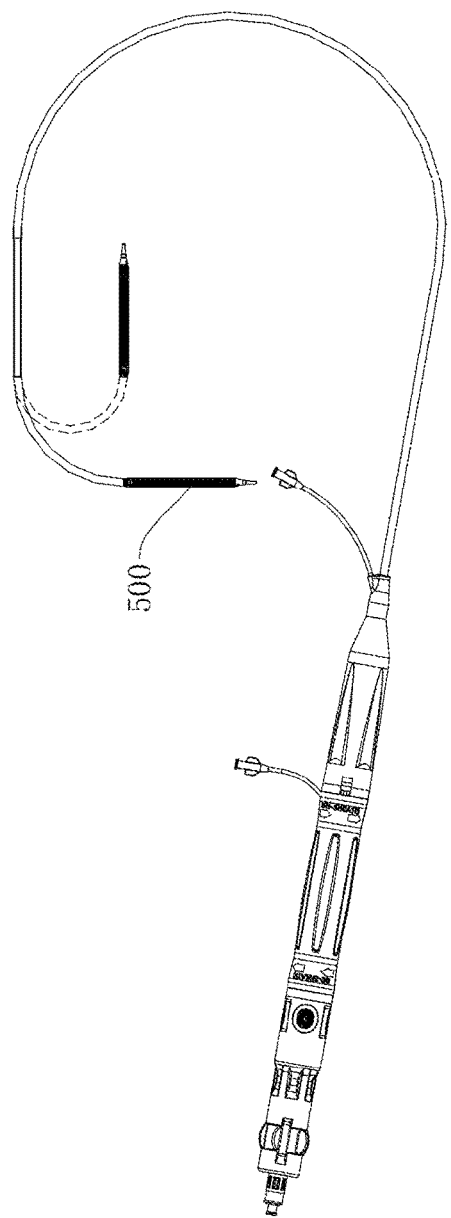
FIG. 35 is a schematic diagram showing the change of a distal end when the delivery system undergoes bending adjustment in the present invention.
Figure 37:
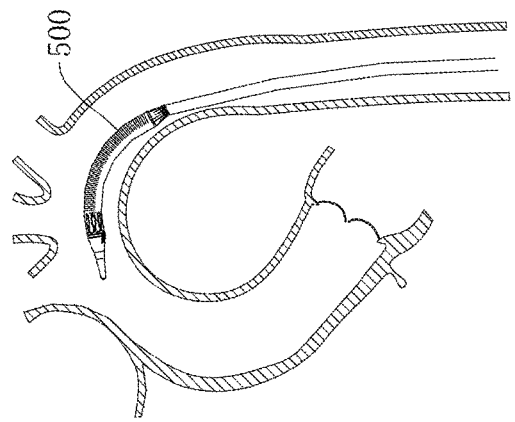
FIGS. 36 to 40 are schematic diagrams showing the state changes of the delivery system according to the present application in different stages in use.
Figure 36:
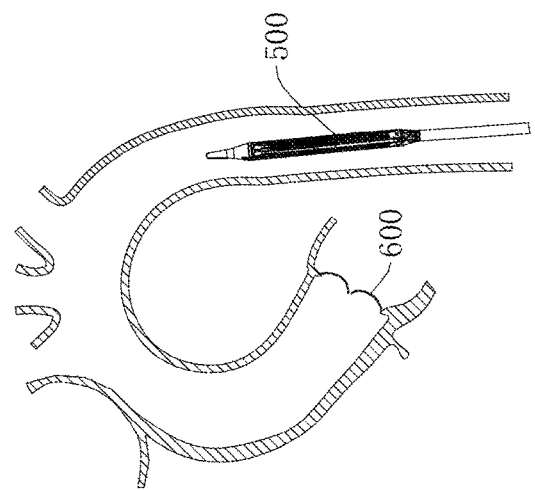
Figure 40:
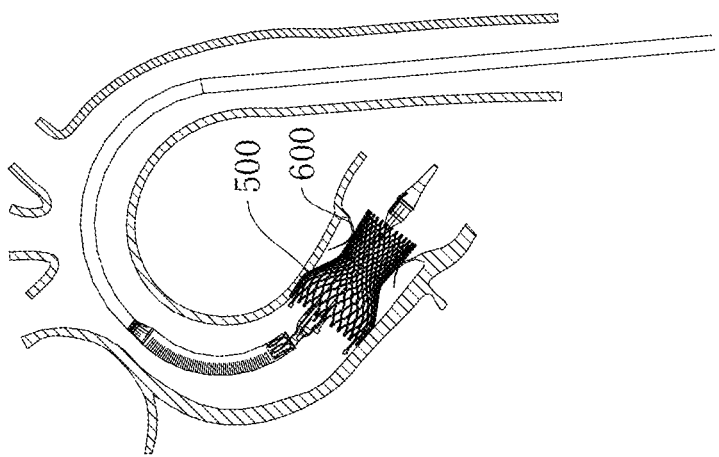
Figure 39:
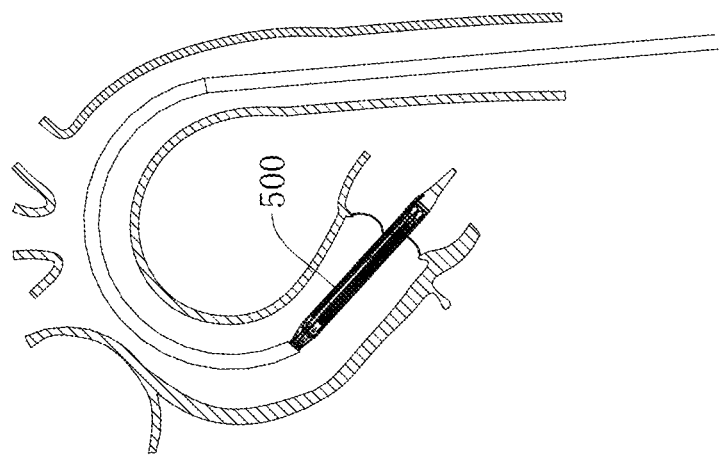
Figure 38:
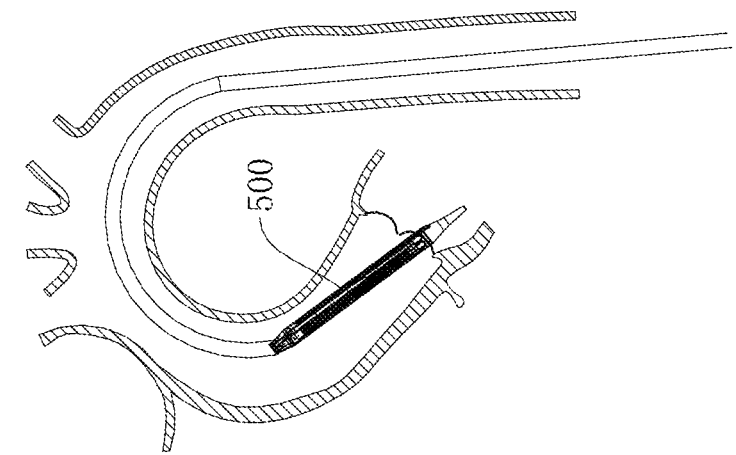

Referring to FIGS. 16 to 17d, according to one embodiment, the nesting relation of the sheath 300 and the core tube component 420, and the release process of the interventional instrument, are illustrated. FIG. 15d also illustrates the approximate axial positional relationships of various sections of the sheath 300 and the core tube component 420. The sheath 300 has a multi-layer composite structure in each section. That is, for a certain section, a multi-layer structure is adopted which includes different parts during processing. The structure of the sheath 300 and the manufacturing process are also one of the improvements of this application. In this embodiment, the core tube component 420 includes the core tube 425. The locking member 422 is fixed on the core tube 425. The distal end of the core tube 425 further extends out of the locking member 422, and the guide head 421 is fixed at the most distal end. A distal end of the guide head 421 has a conical-shaped head structure to facilitate travel in the human body. A position between the guide head 421 and the locking member 422 is configured as the loading position for the interventional instrument. The compressed interventional instrument is located at this position, fitted to and restrained by the locking member 422.

In one embodiment, the core tube 425 is provided therein with the inner core 424 extending therethrough. The distal end of the inner core 424 extends out of the locking member 422 and is fixed to the guide head 421. The distal end of the core tube 425 extends just to the locking member 422. The extension length of the proximal end of the inner core 424 is not strictly limited. Since the core tube 425 does not extend to the loading position, and the inner core 424 has a smaller outer diameter compared with the core tube 425, the radial space of the loading position can be increased.

An embodiment of the present application provides a sheath for delivering an interventional instrument. A distal end of the sheath is the loading section 310 configured for accommodating the interventional instrument. The loading section 310 has a multi-layer structure and includes, from an inner side to an outer side, an inner lining tube 375, a (partial) metal tube 390, and an outer wrapping membrane 380. The metal tube 390 includes, from a proximal end to a distal end, a main tube 350 and a head tube 340 connected end-to-end.

The head tube 340 comprises a body section 346, a plurality of expansion pieces 344 circumferentially arranged on the body section at a distal end thereof at intervals, and a first connector 343 at a proximal end of the body section. A distal end of the main tube 350 is provided with a second connector, and the first connector 343 and the second connector 351 are fitted with each other through form-fitting.

In one embodiment of the present application, portions of the sheath other than the loading section are further improved and illustrated. In this embodiment, the sheath includes, from the proximal end to the distal end, the loading section 310, the bendable section 320, and the first extension section 330 in sequence in an axial direction. The loading section 310 is configured for accommodating an interventional instrument 500. The sheath has a multi-layer structure and includes:

an inner sheath 370, distributed in the bendable section and the first extension section in the axial direction;

an inner lining tube 375, connected end-to-end to a distal end of the inner sheath 370, and distributed in the loading section in the axial direction;

a metal tube 390, surrounding outer peripheries of the distal portion of the inner sheath and the inner lining tube, and distributed in the bendable section and the loading section in the axial direction, wherein a main tube 350 and a head tube 340 are located in the loading section; and an outer wrapping membrane 380, wrapped around the outer periphery of the metal tube 390, and distributed in the bendable section and the loading section in the axial direction.

The loading section 310 needs to surround the interventional instrument, and thus the loading section 310 has a larger diameter than the portions of the sheath at a proximal end of the loading section 310, i.e., the bendable section 320 and the first extension section 330.

FIG. 18 shows some parts of the sheath 300 which are visible. The distal portion of the sheath 300 generally has at least three layers. The inner and outer layers are made of polymer materials, and the intermediate layer is a metal tube 390. The intermediate layer has three sections connected end-to-end, which are, from a distal end to a proximal end, a head tube 340, a main tube 350, and an extension tube 360 sequentially connected end-to-end. In the axial direction, the head tube and the main tube are both distributed in the loading section, and the extension tube is distributed in the bendable section. In the above embodiment, the metal tube 390 is also mentioned when the loading section 310 is described, because the loading section is part of the entire metal tube 390 and only includes the head tube 340 and the main tube 350, which can also be understood as "part" of the entire metal tube 390.

The bendable section can be bent to change the orientation of the distal end of the sheath during delivery. The first extension section mainly serves to provide sufficient axial pushing force and pulling force, and has a sufficient length to connect to the operating handle.

The head tube 340 is formed by cutting a nickel-titanium alloy tube. The main tube 350 and the extension tube 360 are each formed by cutting a stainless steel tube. The head tube 340 and the main tube 350 have larger diameters than the extension tube 360 as they need to enclose the interventional instrument. Referring to the axial positional relationships shown in FIG. 18, it can be seen that the joint portion of the main tube 350 and the extension tube 360 is flared accordingly and has a diameter that increases gradually.

Referring to FIG. 19a, in one embodiment, the distal end of the head tube 340 is provided with a plurality of spaced openings 341 along the circumferential direction. Each expansion piece 344 is located between two adjacent openings, and each expansion piece 344 has a hollow area 345. In a preferred embodiment, the expansion pieces 344 are arranged evenly in the circumferential direction, and the number of the expansion pieces ranges between 3 to 6, for example, 5 expansion pieces may be provided.

Generally, the head tube 340 is preferably a single piece. The body section 346 forms a hollow imaging area 342, where imaging points are provided. The first connector 343 is T-shaped and is connected to the main tube 350 for axially positioning. Both the body section 346 and the first connector 343 are provided with through holes 347 to allow the polymer materials of the inner layer and the outer layer of the sheath to be properly combined.

The openings 341 are elongated gaps, each having an open distal end and a closed proximal end. As the head tube 340 is made of elastic metal materials such as Nitinol, each expansion piece 344 is able to flare radially outwardly, to adapt to the gradual deformation of the interventional instrument when the interventional instrument is released, and to prevent the interventional instrument from suddenly popping out at the end of the release process. Further, when withdrawn, the expansion pieces 344 flare radially outwardly to form a flared opening, which is convenient for guiding the interventional instrument to be gradually compressed radially and retracted into the sheath 300. In order to obtain better elasticity, the head tube 340 may be made of Nitinol, and each expansion piece attains a converged configuration extending in the axial direction of the sheath and a flared configuration away from each other.

The hollow area 345 of the expansion piece 344 facilitates the deformation of the expansion piece, reducing the resistance for flaring outwardly. In one embodiment, the hollow area 345 may be in the form of an elongated hole extending along the axial direction of the head tube 340. Within the same expansion piece, one, two or more elongated holes may be provided.

In a preferred embodiment, the elongated hole extends with a consistent width. Two ends of the elongated hole in its longitudinal direction have arc-shaped inner edges, which can avoid cracking caused by excessive stress concentration during deformation.

In one embodiment, each expansion piece 344 has a narrowed portion 348 at a proximal end portion, and the opening has a widened portion at a proximal end portion corresponding to the narrowed portion 348.

To decentralize the stress, the contour of the widened portion is smoothly curved, such as the shape of a larger end of a drop shape.

In one embodiment, the opening substantially extends with a consistent width, except for the chamfering of the distal end which is adapted to the expansion piece and the widened portion of the proximal end.

The consistent width of the opening is approximately equal to the width of the elongated hole. For example, if the width of the elongated hole is taken as a reference width, then the consistent width of the opening is the reference width ±20%.

To allow the expansion pieces 344 to flare outwardly easily at the narrowed portion 348 and reduce the deformation resistance of the proximal ends of the narrowed portion, in one embodiment, the proximal end 349 of the elongated hole extends beyond the narrowed portion of the expansion piece. In a preferred embodiment, the proximal end 349 of the elongated hole extends beyond the narrowed portion of the expansion piece by 1 to 5 mm, for example, 1.5 to 3 mm.

To avoid potential harm, in one embodiment, the distal end of the expansion piece has a smooth outer edge, for example, in a fillet form or it as a whole has a circular arc shape protruding distally.

Referring to FIG. 19b, in one embodiment, each expansion piece 344 has a hollow area 345, which has a plurality of through holes arranged along the axial direction of the sheath at intervals. The total area of the through holes within each expansion piece is smaller than 50% of the area of the expansion piece. As can be seen, on the same expansion piece, the through hole has a larger area closer to the distal end. The through hole may be circular or elliptical, and 2 to 5 through holes may be provided on an individual expansion piece.

Similar to the embodiment shown in FIG. 19a, the body section 346 of the head tube 340 forms a hollow imaging area 342, where imaging points are provided. The first connector 343 is T-shaped and is connected to the main tube for axial positioning. Both the body section 346 and the first connector 343 are provided with through holes, to allow the polymer materials of the inner layer and the outer layer of the sheath to be properly combined. Two adjacent expansion pieces 344 are spaced with an opening 341 defined therebetween. The openings 341 are elongated gaps, each having an open distal end and a closed proximal end. The expansion piece 344 becomes narrower closer to the distal end. The most distal end of the expansion piece has a curved edge to improve the safety.

To prevent the metal material of the intermediate layer from scratching the inner wall of the blood vessel, the outermost layer wraps the head tube 340, the main tube 350 and the extension tube 360. The outer wrapping membrane 380 of the outermost layer can be made of a polymer material. Since the metal portion has multiple sections, the outer wrapping membrane 380 also has multiple sections which are connected one another and melted together during processing.

For example, along the axial direction of the sheath, the outer wrapping membrane 380 includes multiple sections, and the sections are made of different materials, or at least two of them are made of a same material.

In one embodiment, the strength of the outer wrapping membrane corresponding to the main tube 350 is greater than the strength of the outer wrapping membrane corresponding to the distal end of the head tube 340.

The inner layer includes the inner sheath 370 and the inner lining tube 375. One end of the inner sheath 370 extends proximally, and the other end extends to the joint portion of the main tube 350 and the extension tube 360. The inner lining tube 375 further extends distally from the joint portion of the main tube 350 and the extension tube 360 to reach the distal side of the head tube 340, wherein the inner lining tube 375 can be made of PTFE.

The axial position of the distal portion of the extension tube 360 corresponds to the compliant section 4251 and the first pulling section 411, and the extension tube 360 can also form a reinforcing rib by cutting.

Referring to FIGS. 20 to 24, the inner sheath 370 has a multi-layer structure, and includes, from an inside to an outside, an inner layer 3701 of PTFE, a woven layer 3702, a woven layer 3704, and an outer layer 3705. Two reinforcing ribs 3703 extending in the axial direction are fixedly sandwiched between the woven layer 3702 and the woven layer 3704.

One of the two reinforcing ribs 3703 is located at the same circumferential position as the reinforcing rib 4253, and the circumferential position of the other reinforcing rib 3704 is offset from that of the reinforcing rib 4253 by 180 degrees.

The woven layer 3702 and the woven layer 3704 are not required to have an obvious contour, and may be woven as one piece with the reinforcing ribs 3703 sandwiched therein. The outer layer 3705 may be made of Pebax.

The reinforcing rib 4253 provided in the compliant section 4251 and the reinforcing rib 4111 provided in the first pulling section 411 are circumferentially offset by 180 degrees.

The cross-sectional view only shows the extension tube 360 of the sheath. The extension tube 360 may be provided with a reinforcing rib 3601, which is radially aligned with the reinforcing rib 4253, that is, the reinforcing rib 3601 and the reinforcing rib 4253 are located at the same circumferential position.

In another embodiment, the extension tube 360 may be provided with two reinforcing ribs, namely a reinforcing rib 3601 and a reinforcing rib 3602. The reinforcing rib 3601 is radially aligned with the reinforcing rib 4253, that is, they are located at the same circumferential position. The reinforcing rib 3602 is aligned with the reinforcing rib 4111, that is, they are located at the same circumferential position which is offset from that of the reinforcing rib 4253 by 180 degrees.

The inner sheath 370 exists not only in the bendable section 320 but also in the first extension section 330. As the bendable section 320 has a larger bending angle during bending adjustment, the inner sheath 370 has different strengths in the bendable section 320 and in the first extension section 330. The inner sheath 370 is softer in the bendable section 320. For example, the outer layer 3705 of the inner sheath 370 at the bendable section 320 is made of Pebax of 30-59D, and the outer layer 3705 of the inner sheath 370 at the first extension section 330 is made of Pebax of 60-90D. The woven layer and the PTFE inner layer 3701 of the inner sheath 370 at different sections can have the same configurations. Referring to FIGS. 25 to 34, an embodiment of the present application provides a method for processing the sheath 300, which includes the following steps.

Step S100: forming a flared portion at a distal end of an inner sheath.

Specifically, the end portion, i.e., the distal end 371, of the inner sheath can be softened by heating and followed by inserting a core rod 372 to expand the diameter of the distal end 371 to form a flared portion 374. A part of the outer periphery of the core rod 372 can be processed into a truncated cone section 373 corresponding to an expected shape of the flared portion 374.

Step S200: mounting an inner lining tube around the outer periphery of the flared portion.

Specifically, an inner lining tube 375 made of PTFE is provided, which has ears arranged at intervals along the circumferential direction at one end, with cut areas 376 formed between the ears. This end of the inner lining tube 375 is mounted around the flared portion 374 and is then surrounded with a fixing sleeve 377 and heat-melted, such that the inner lining tube 375 is connected to the distal end 371 of the inner sheath.

The fixing sleeve 377 and the flared portion 374 are made of the same material, such as Pebax, etc. The cut areas 376 facilitate the fusion of the fixing sleeve 377 and the flared portion 374, thereby ensuring the connection strength of the inner lining tube 375.

Step S300: mounting a metal tube 390 around the outer peripheries of the inner sheath and inner lining tube.

Specifically, an extension tube 360, a main tube 350, and a head tube 340 are connected end-to-end in sequence. Adjacent tubes 360, 350, 340 are axially positioned by hooking or snap-fitting. The head tube 340 is a nickel-titanium alloy tube, and the extension tube 360 and the main tube 350 may be stainless steel tubes.

The proximal end of the head tube 340 has T-shaped first connectors 343, and the distal end of the main tube 350 has T-shaped second connectors 351. The first connectors 343 and the second connectors 351 are fitted with each with complementary shapes and are axially positioned.

The proximal end of the main tube 350 has a converged port 352, and is connected to the extension tube 360 through the converged port 352 by conventional means such as hooking or snap-fitting. The wall of the main tube 350 is provided with a hollow area 353 and a hollow area 354, with a guide rib 355 which extends axially located therebetween. The guide rib 355 can limit the bending direction of the sheath 300. In this embodiment, two guide ribs 355 are provided which are radially opposite to each other.

The extension tube 360, the main tube 350, and the head tube 340 are connected end-to-end in sequence and then mounted outside the inner sheath 370 and the inner lining tube 375. The axial position of the flared portion 374 corresponds to the axial position of the converged port 352. The inner lining tube 375 is slightly longer than the head tube 340. The portions of the inner lining tube 375 corresponding to the openings 341 are also cut for deformation of the expansion piece.

Step S400: wrapping the outer surface of the metal tube 390 segmentally with an outer wrapping material, to form an outer wrapping membrane after the outer wrapping material in each section are heat melted. Specifically, the step S400 includes the following steps.

Step S410: wrapping the joint portion of the main tube 350 and the head tube 340 with a first connecting sleeve 381, wrapping the head tube 340 with a head sleeve 382, and the first connecting sleeve 381 and the head sleeve 382 are fixed by heat melting.

The head sleeve 382 is slightly longer than the head tube 340 and is substantially aligned with the inner lining tube 375. Then, the first connecting sleeve 381 and the head sleeve 382 together with a corresponding portion of the inner lining tube 375 are heat melted, to fix the joint portion of the main tube 350 and the head tube 340 and the head tube 340 by wrapping.

A first lining 383 and a second lining 384 are respectively placed at the hollow area 353 and the hollow area 354, and then heat melted with corresponding positions of the inner lining tube 375. The melted first lining 383 and second lining 384 are filled into the corresponding hollow areas.

Step S420: wrapping the outer periphery of the main tube 350 with a main sleeve 385 and fixing it by heat melting.

A distal end of the main sleeve 385 is substantially aligned with a proximal end of the first connecting sleeve 381, and a proximal end of the main sleeve 385 encloses the joint portion of the extension tube 360 and the main tube 350.

The head sleeve 382 is required to have a good flexibility, and may be made of TPU. However, the first connecting sleeve 381, the first lining 383, the second lining 384, and the main sleeve 385 can be made of Pebax with a high strength. The first lining 383 and the second lining 384 have a smaller thickness than the main sleeve 385. For example, the thickness of the first lining 383 and the second lining 384 is about 0.15 mm, and the thickness of the main sleeve 385 may be increased up to 0.35 mm.

In addition, the first connecting sleeve 381 is required to have a significant strength, and thus may be made of a relatively hard material with, for example, a hardness of 60 to 72D. The main sleeve 385 mainly serves as a wrap for protection, and its hardness may be appropriately reduced to, for example, 40 to 55D.

Step S430: wrapping the proximal end of the extension tube 360 and a portion of the inner sheath 370 adjacent thereto with a second connecting sleeve 386 and fixing it by heat melting.

Step S440: wrapping the outer periphery of the extension tube 360 with a connecting sleeve 387, and fixing it by heat melting.

The connecting sleeve 387 is axially positioned such that a proximal end thereof is connected to the second connecting sleeve 386 and a distal end thereof is connected to the main sleeve 385.

The second connecting sleeve 386 is made of Pebax with a higher strength. The connecting sleeve 387 is located at a bendable position and thus needs to have better flexibility, and can be made of TPU. In addition, the connecting sleeve 387 also prevents the internal metal tube 390 from directly contacting and scratching the blood vessel wall, as well as providing a sealing function.

The materials wrapping the outer peripheries of the extension tube 360, the main tube 350, and the head tube 340 are finally melted together and form the outer wrapping membrane 380, and the portion at the end thereof that extends beyond the distal end of the head tube 340 is heat-melted and sealed. The portions corresponding to the openings 341 can be cut accordingly to adapt to the possible deformation at the openings 341. Alternatively, the possible deformation at the openings 341 may be adapted to by the elasticity of the material of the head sleeve 382.

Referring to FIGS. 35 to 40, during use, the bending adjustment system of the present application is able to actively change the orientation of the distal portion by pulling the bendable adjustable tube with the operating handle, thus facilitating the delivery of an interventional instrument 500 within a complex path. For example, when an interventional instrument 500 is being delivered to the location of a native aortic valve 600, the distal end of the sheath assembly is allowed to be orientated with, and placed in, the aortic valve 600 by bending adjustment when passing through an aortic arch. Because it is the core tube component that is pulled by the bendable adjustable tube, when the interventional instrument is released by withdrawing the sheath, the orientation of the interventional instrument loaded on the core tube component is kept unchanged, thus avoiding a potential risk of incorrect positioning during the release process.

The features described in the above various embodiments may be combined. In order to simplify the descriptions, not all possible combinations of the features in the above embodiments have been described. However, any combinations of the features should be within the scope of the disclosure as long as no conflict resides between these features. In the case where the features in different embodiments are shown in the same drawing, it may be considered that this drawing discloses a combination of the various embodiments involved.

The above embodiments are only several implementations of the present application, which are described specifically and in detail, without limitation to the scope claimed by the present application. It should be noted that those skilled in the art can make various modifications and variations to the embodiments without departing from the spirit and scope of the present application, and these modifications and variations should fall into the scope claimed by the present application.

What is claimed is:

1. A sheath for delivering an interventional instrument, comprising, from a distal end to a proximal end, a distal end as a loading section for accommodating the interventional instrument, a bendable section, and a first extension section in sequence in an axial direction, the loading section having a larger diameter than the bendable section and the extension section, wherein the sheath has a multi-layer structure and comprises, from inside to outside, an inner layer, a metal tube and an outer wrapping membrane fixedly connected together; the inner layer comprises an inner lining tube distributed in the loading section, and an inner sheath connected to the inner lining tube and distributed in the bendable section and the first extension section, the inner sheath is softer in the bendable section than in the first extending section; the metal tube comprises, from a distal end to a proximal end, a head tube, a main tube and an extension tube connected one another, wherein the head tube and the main tube are mounted around the inner lining tube, and the extension tube is distributed in the bendable section and mounted around the inner sheath, the outer wrapping membrane is wrapped around an outer periphery of the metal tube; and the head tube comprises a body section, a plurality of elastic expansion pieces arranged circumferentially in intervals on the body section at a distal side thereof.

2. The sheath for delivering an interventional instrument according to claim 1, wherein each expansion piece has a hollow area; the hollow area comprises a plurality of through holes arranged in intervals in an axial direction of the sheath, and the total area of the through holes on each expansion piece is less than 50% of the area of the respective expansion piece.

3. The sheath for delivering an interventional instrument according to claim 2, wherein the hollow area comprises an elongated hole, and the elongated hole extends along an axial direction of the head tube.

4. The sheath for delivering an interventional instrument according to claim 1, wherein there is an opening between two adjacent expansion pieces, each expansion piece has a narrowed portion at a proximal portion thereof, and each opening has a widened portion at a proximal portion thereof corresponding to the narrowed portion.

5. The sheath for delivering an interventional instrument according to claim 4, wherein a contour of the widened portion is smoothly curved.

6. The sheath for delivering an interventional instrument according to claim 4, wherein a middle portion the opening in a longitudinal direction thereof has a consistent width; and the consistent width of the opening is substantially equal to a width of the elongated hole.

7. A sheath assembly, comprising a sheath for delivering an interventional instrument according to claim 1; and a core assembly, wherein the sheath and the core assembly are slidably nested within each other, and the core assembly comprises a core tube with a distal portion mounted with a locking member for connecting an interventional instrument.

8. The sheath assembly according to claim 7, wherein the core assembly further comprises a bendable adjustable tube mounted around an outer periphery of the core tube; and the distal ends of the bendable adjustable tube and the core tube are fixedly connected to each other, and the proximal ends of the bendable adjustable tube and the core tube are slidable relative to each other; or
wherein the core assembly further comprises a bendable adjustable tube inside the core tube; and the distal ends of the bendable adjustable tube and the core tube are fixedly connected to each other, and the proximal ends are slidable relative to each other.

9. The sheath assembly according to claim 8, wherein the core tube comprises a compliant section adjacent to the locking member and a third extension section connected end-to-end to the compliant section and extending proximally, wherein the compliant section is a hypotube with a length ranging from 120 to 180 mm, and the third extension section is a wire casing or a hypotube.

10. The sheath assembly according to claim 9, wherein the bendable adjustable tube comprises, from a distal end to a proximal end, a pulling section and a second extension section in sequence, wherein the pulling section is a single piece and is a hypotube; and the pulling section comprises, from a distal end to a proximal end, a first pulling section, a transition section and a second pulling section, in which the first pulling section has higher flexibility than the second pulling section, and a ratio of a length of the first pulling section to a length of the compliant section is 1:0.7 to 1.5.

11. The sheath assembly according to claim 10, wherein the compliant section forms a first reinforcing rib extending axially by cutting; and a width of a cut slit in the compliant section ranges from 0.1 to 1 mm, and a slit spacing ranges from 0.1 to 1 mm.

12. The sheath assembly according to claim 11, wherein the compliant section has an extreme radius of curvature that, after bending, is smaller closer to the distal end.

13. The sheath assembly according to claim 11, wherein the first pulling section forms an axially extending second reinforcing rib by cutting, and a circumferential position of the second reinforcing rib is offset from a circumferential position of the first reinforcing rib by 180 degrees.

14. The sheath assembly according to claim 13, wherein a width of a cut slit in the first pulling section ranges from 0.03 to 0.5 mm, and a slit spacing ranges from 0.2 to 0.85 mm.

15. The sheath assembly according to claim 13, wherein the second pulling section forms two axially extending third reinforcing ribs by cutting, and the two third reinforcing ribs are radially opposite to each other, and the two third reinforcing ribs having circumferential positions that are offset from the circumferential position of the first reinforcing rib by 90 degrees.

16. The sheath assembly according to claim 15, wherein in the second pulling section, a width of a cut slit ranges from 0.03 to 0.5 mm, and a slit spacing ranges from 0.2 to 0.85 mm; and wherein the transition section has an uncut structure that is a complete ring in the circumferential direction.

17. The sheath assembly according to claim 11, wherein the sheath comprises, from a distal end to a proximal end, a loading section, a bendable section, and a first extension section in sequence in an axial direction, wherein
a proximal end of an inner lining tube is connected end-to-end to an inner sheath, and the inner sheath is axially distributed in the bendable section and the first extension section;
a proximal end of a main tube is connected to an extension tube made of a metal material, and the extension tube is axially distributed in the bendable section; and
an outer wrapping membrane extends proximally and wraps around an outer periphery of the extension tube.

18. The sheath assembly according to claim 17, wherein the inner sheath has a multi-layer structure, with two fourth reinforcing ribs extending axially provided in an interlayer, wherein one of the fourth reinforcing ribs is at the same circumferential position as the first reinforcing rib, and the other of the fourth reinforcing ribs is at a circumferential position offset from the circumferential position of the first reinforcing rib by 180 degrees.

19. The sheath assembly according to claim 17, wherein the extension tube is a hypotube in which at least one fifth reinforcing rib extending axially is provided,
wherein the at least one fifth reinforcing rib is at the same circumferential position as the first reinforcing rib; or two fifth reinforcing ribs are provided, with one of the fifth reinforcing ribs at the same circumferential position as the first reinforcing rib, and the other of the fifth reinforcing ribs is at a circumferential position offset from the circumferential position of the first reinforcing rib by 180 degrees.

* * * * *